(12) United States Patent
Doudareva et al.

(10) Patent No.: US 6,558,922 B1
(45) Date of Patent: May 6, 2003

(54) METHODS AND COMPOSITIONS FOR PRODUCTION OF FLORAL SCENT COMPOUNDS

(75) Inventors: Natalia Doudareva, Lafayette, IN (US); Lisa M. Murfitt, West Lafayette, IN (US)

(73) Assignee: Purdue Research Foundation, W. Lafayette, IN (US)

(*) Notice: Subject to any disclaimer, the term of this patent is extended or adjusted under 35 U.S.C. 154(b) by 142 days.

(21) Appl. No.: 09/653,375

(22) Filed: Sep. 1, 2000

Related U.S. Application Data

(60) Provisional application No. 60/152,393, filed on Sep. 3, 1999.

(51) Int. Cl.[7] .......................... C12P 21/02; A01H 5/00; C12N 1/21; C12N 5/10; C12N 15/29; C12N 15/63
(52) U.S. Cl. .................... 435/69.1; 435/243; 435/252.3; 435/320.1; 435/325; 435/410; 536/23.6; 800/295
(58) Field of Search .......................... 536/23.6; 435/193, 435/243, 252.3, 410, 325, 69.1, 320.1; 800/295

(56) References Cited

U.S. PATENT DOCUMENTS 5,849,526 A 12/1998 Pichersky

OTHER PUBLICATIONS

Wang et al., *Floral Scent Production in Clarkia breweri (Onagraceae)*, Plant Physiol. (1997) 114:213–221.
Bushue et al., *Floral Scent Production in Antirrhinum majus.* Published in Jul. 1999 Meeting Abstract Booklet of the Phytochemical Society of North America, Evolution of Metabolic Pathways Conference, Concordia University, Montreal, Canada p. 80, Poster 289, (Jul. 1999).
Joshi, Chandrashekhar P. and Chiang, Vincent L., *Conserved Sequence Motifs in Plant S–adenosyl–L–methionine–dependent Methyltransferases*, Plant Molecular Biology, (1998) 37: 663–674.
Bushue, et al., New Class of Plant Methyltransferases:Benzoic Acid Carboxyl Methyltransferase from Snapdragon Flowers, Published in Jul. 1999 Meeting Abstract Booklet of the American Society of Plant Physiology, Baltimore Maryland, p. 32.
Ibrahim, et al., *Plant O–methyltransferasess: Molecular Analysis, Common Signature and Classification*, Plant Molecular Biology (1998) 36: 1–10.
Dudareva, et al., *Floral Scent Production in Clarkia breweri*, Plant Physiol. (1998) 116: 599–604.
Knudsen, et al., *Flora Scents—A Checklist of Volatile Compounds Isolated by Head–Space Techniques*, Phytochemistry, (1993) vol. 33, No. 2, 253–280.
Dudareva, et al., *Developmental Regulation of Methyl Benzoate Biosynthesis and Emission in Snapdragon Flowers*, The Plant Cell (2000), vol. 12, 949–961.
Ross, et al., *S–Adenosyl–L–Methionine: Salicylic Acid Carboxyl Methyltransferase, an Enzyme Involved in Floral Scent Production and Plant Defense, Represents a New Class of Plant Methyltransferases*, Archives of Biochemistry and Biophysics (1999) vol. 367, No. 1, 9–16.
Dudareva, N. and Pichersky, E., (2000) "Biochemical and Molecular Genetic Aspects of Floral Scents" *Plant Physiology* 122:627–633.

Primary Examiner—Terry McKelvey
(74) Attorney, Agent, or Firm—Greenlee Winner & Sullivan PC

(57) ABSTRACT

Purified BAMT proteins that function in floral scent production are provided. The proteins are enzymes that advantageously function in the formation of floral scent compounds, such as methyl benzoate. Nucleotide sequences encoding functional BAMT proteins are also provided. The invention also provides recombinant vectors including the nucleotide sequence encoding BAMT, host cells that include the recombinant vectors described herein, transgenic plants, methods of expressing proteins, including BAMT, and methods of transforming host cells.

44 Claims, 13 Drawing Sheets

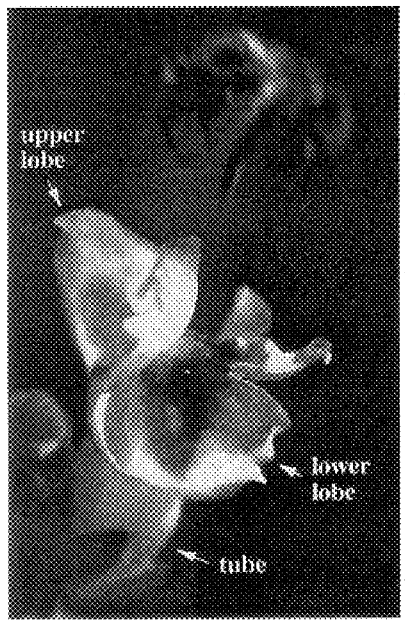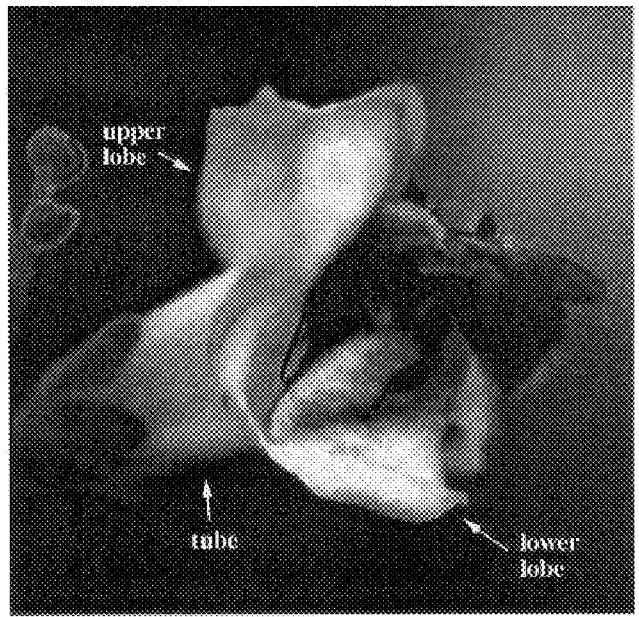
Fig. 3A    Fig. 3B
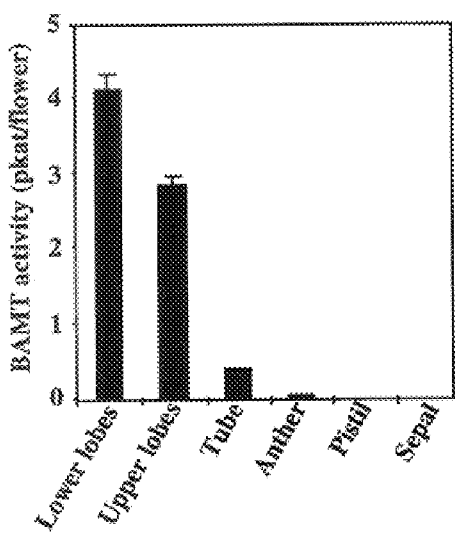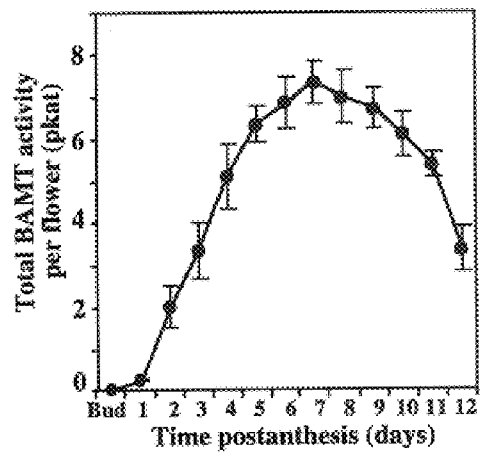
Fig. 3C    Fig. 3D

```
BAMT        1    ---MKVMKKLLCMNIAGDGETSYANNSGLQKVMMSKSLHVLDETLKDIIGDHVGFPKCFKM
SAMT        1    ---MDVRQVLHM-KGGAGENSYAMNSFIQRQVISITKPITEAAITALYSGDTVTTR-LAT
Z997081     1    MDKKDMEREFYM-TGGDGKTSYARNSSLQKKASDTAKHITLETLQQLY--KETRPKSLGI
AC006528l   1    ----------M-KGGTGDHSYATNSHYQRSVFYEIQPLVIENVREMLL-KNGFPGCIKV

BAMT       59    MDMGCSSGPNALLVMSGIINTIEDLY-TEKNINELPEFEVFLNDLPDNDFNNLFKLLSHE
SAMT       56    ADLGCSSGPNALFAVTELIKTVEELR-KKMGRENSPEYQIFLNDLPGNDFNAIFRSLPIE
Z997081    58    ADLGCSSGPNTLSTITDFIKTVQVAHHREIPIQPLPEFSIFLNDLPGNDFNFIFKSLPDF
AC006528l  48    ADLGCSTGQNTVLAMSAIAYTIMESY-QQMSKNP-PEIDCYLNDLPENDFNTTFKLFHSF

BAMT      118    N------------GNCFVYGLPGSFYGRLLPKKSLHFAYSSYSIHWLSQVPEGLED----
SAMT      115    NDVD---------GVCFINGVPGSFYGRLFPRNTLHFIHSSYSLMWLSQVPIGIE-----
Z997081   118    HIELKRDNNNGDCPSVFIAAYPGSFYGRLFPENTIHFVYASHSLHWLSKVPTALYDEQGK
AC006528l 106    QEKLKP----EVKGKWFVSGVPGSFYSRLFPRKSLHFVHSAFSIHWLSRIPDGLE-----

BAMT      162    -NNRQNIYMATESPPEVYKAYAKQYERDFSTFLKLRGEEIVPGGRMVLTFNGRSVEDPSS
SAMT      161    -SNKGNIYMANTCPQSVLNAYYKQFQEDHALFLRCRAQEVVPGGRMVLTILGRRSEDRAS
Z997081   178    SINKGCVSICSLSSEAVSKAYCSQFKEDFSIFLRCRSKEMVSAGRMVLIILGREGPDHVD
AC006528l 157    -SNTKSTHIKYPYPSNVYKSYLNQFKIDFSLFLKMRSEEVVHNGHMVLTFVGRKVSDTLS

BAMT      221    KDDLAIFTLLAKTLVDMVAEGLVKMDDLYSFNIPIYSPCTREVEAAILSEGSFTLDRLEV
SAMT      220    TECCLIWQLLAMALNQMVSEGLIEEEKMDKFNIPQYTPSPTEVEAEILKEGSFLIDHIEA
Z997081   238    RGNSFFWELLSRSIADLVAQGETEEEKLDSYDMHFYAPSADEIEGEVDKEGSFELERLEM
AC006528l 216    KDCFQVWSLLSDCLLDLASEGFVNDSMVKSFNMPFYNPNEEEVREFILKEGSFEITKIEK

BAMT      281    FRVCWDASDYTDDDDQQDPSIFGKQRSGKFVADCVRAITEPMLASHFGSTIMDLLFGKYA
SAMT      280    SEIYWSS--CTKDGDG-GGSVE---EEGYNVARCMRAVAEPLLLDHFGEAIIEDVFHRYK
Z997081   298    LEVKKDK-----GNT-EGDIS----YGKAVAKTVRAVQESMLVQHFGEKILDKLFDTYC
AC006528l 276    FDHVVPYKIDREEEDE-EQSLQ--LEAGIKHASWARCITEPLLVAHFGDAIIEPVFNKYA

BAMT      341    KKIVEHLSVENSS---YFSIVVSLSRR--
SAMT      334    LLIIERMSKEKTK---FINVIVSLIRKSD
Z997081   347    RMVDDELAKEDIR---PITFVVVLRKKL-
AC006528l 333    HYMAKYLSVSNHRRNMTLVIVVSLTRK--
```

*Fig. 4*

SEQUENCE LISTING

```
<160> NUMBER OF SEQ ID NOS: 10

<210> SEQ ID NO 1
<211> LENGTH: 1363
<212> TYPE: DNA
<213> ORGANISM: Antirrhinum majus
<220> FEATURE:
<221> NAME/KEY: CDS
<222> LOCATION: (19)..(1110)

<400> SEQUENCE: 1
gccggacgcc aaagaaaa atg aaa gtg atg aag aaa ctt ttg tgt atg aat        51
                    Met Lys Val Met Lys Lys Leu Leu Cys Met Asn
                     1               5                      10 att gca gga gat ggt gaa act agc tac gcc aac aat tct ggc ctt caa        99
Ile Ala Gly Asp Gly Glu Thr Ser Tyr Ala Asn Asn Ser Gly Leu Gln
             15                  20                  25 aaa gtt atg atg tca aaa tca ttg cat gtt tta gac gaa acc ctt aaa       147
Lys Val Met Met Ser Lys Ser Leu His Val Leu Asp Glu Thr Leu Lys
     30                  35                  40 gat att atc ggt gat cat gtt ggc ttc cca aaa tgc ttc aag atg atg       195
Asp Ile Ile Gly Asp His Val Gly Phe Pro Lys Cys Phe Lys Met Met
 45                  50                  55 gat atg ggt tgt tca tca ggg cct aac gcc ctt ttg gtc atg tcc ggc       243
Asp Met Gly Cys Ser Ser Gly Pro Asn Ala Leu Leu Val Met Ser Gly
 60                  65                  70                  75 att ata aat aca att gag gat ttg tac aca gag aag aat att aat gaa       291
Ile Ile Asn Thr Ile Glu Asp Leu Tyr Thr Glu Lys Asn Ile Asn Glu
                 80                  85                  90 tta cct gaa ttt gag gtt ttt ctg aac gat ctt cca gac aac gac ttc       339
Leu Pro Glu Phe Glu Val Phe Leu Asn Asp Leu Pro Asp Asn Asp Phe
             95                 100                 105 aac aac ctc ttc aaa ttg tta tca cat gag aat gga aac tgc ttt gta       387
Asn Asn Leu Phe Lys Leu Leu Ser His Glu Asn Gly Asn Cys Phe Val
        110                 115                 120 tat ggt ttg cct gga tct ttc tac ggg aga cta ttg cca aaa aag agc       435
Tyr Gly Leu Pro Gly Ser Phe Tyr Gly Arg Leu Leu Pro Lys Lys Ser
    125                 130                 135 cta cac ttt gct tat tct tcc tac agt att cac tgg ctc tct cag gtt       483
Leu His Phe Ala Tyr Ser Ser Tyr Ser Ile His Trp Leu Ser Gln Val
140                 145                 150                 155 cct gaa ggg ctg gag gat aat aac aga caa aac att tac atg gca acg       531
Pro Glu Gly Leu Glu Asp Asn Asn Arg Gln Asn Ile Tyr Met Ala Thr
                160                 165                 170 gaa agt cct ccg gaa gtg tac aaa gca tac gca aag caa tac gaa aga       579
```

-continued

```
Glu Ser Pro Pro Glu Val Tyr Lys Ala Tyr Ala Lys Gln Tyr Glu Arg
            175                 180                 185 gac ttc tcc aca ttt cta aag ttg cga ggc gag gaa att gta cca ggt      627
Asp Phe Ser Thr Phe Leu Lys Leu Arg Gly Glu Glu Ile Val Pro Gly
        190                 195                 200 gga cgc atg gtc ttg aca ttt aac ggc aga agt gtt gaa gat ccc tcg      675
Gly Arg Met Val Leu Thr Phe Asn Gly Arg Ser Val Glu Asp Pro Ser
    205                 210                 215 agc aaa gat gac tta gca att ttc aca ttg ctt gca aaa aca cta gtt      723
Ser Lys Asp Asp Leu Ala Ile Phe Thr Leu Leu Ala Lys Thr Leu Val
220                 225                 230                 235 gat atg gtg gct gag ggg ctt gtc aag atg gac gat ttg tac tcg ttt      771
Asp Met Val Ala Glu Gly Leu Val Lys Met Asp Asp Leu Tyr Ser Phe
                240                 245                 250 aac att cct att tac tca cca tgt acg cgc gaa gta gag gca gca att      819
Asn Ile Pro Ile Tyr Ser Pro Cys Thr Arg Glu Val Glu Ala Ala Ile
            255                 260                 265 ctg agt gaa ggg tct ttt acg ttg gac agg cta gag gtc ttt cgt gtt      867
Leu Ser Glu Gly Ser Phe Thr Leu Asp Arg Leu Glu Val Phe Arg Val
        270                 275                 280 tgt tgg gat gca agt gac tac aca gat gac gat gat cag caa gac cca      915
Cys Trp Asp Ala Ser Asp Tyr Thr Asp Asp Asp Gln Gln Asp Pro
    285                 290                 295 tca atc ttt ggc aaa caa agg agt gga aaa ttt gtg gca gat tgt gta      963
Ser Ile Phe Gly Lys Gln Arg Ser Gly Lys Phe Val Ala Asp Cys Val
300                 305                 310                 315 cgg gct att acg gaa cca atg ctg gct agc cat ttt ggg agc act att     1011
Arg Ala Ile Thr Glu Pro Met Leu Ala Ser His Phe Gly Ser Thr Ile
                320                 325                 330 atg gat ctt cta ttt gga aag tat gca aag aaa ata gtg gag cat cta     1059
Met Asp Leu Leu Phe Gly Lys Tyr Ala Lys Lys Ile Val Glu His Leu
            335                 340                 345 tct gtg gag aac tcg tca tat ttc agc ata gta gtt tct cta agt agg     1107
Ser Val Glu Asn Ser Ser Tyr Phe Ser Ile Val Val Ser Leu Ser Arg
        350                 355                 360 aga tgaagtcaac aggatggaga taccacgtat ttcggcacat ttgctgtaaa          1160
Arg atgatgatat aattatagaa taaaattata ttgaatgcag aataattgtg tcgcacacca   1220
ttgtttccaa tactatctac atgcaattgt taattcagtt tttgattttg cttcttctct   1280
ttctaatact gttctttttgt tgcagaggtg tgaactgatc agcacctata tatagtacta  1340
tttttatagc agaagtaatg gaa                                          1363

<210> SEQ ID NO 2
<211> LENGTH: 364
<212> TYPE: PRT
<213> ORGANISM: Antirrhinum majus

<400> SEQUENCE: 2

Met Lys Val Met Lys Lys Leu Leu Cys Met Asn Ile Ala Gly Asp Gly
  1               5                  10                  15

Glu Thr Ser Tyr Ala Asn Asn Ser Gly Leu Gln Lys Val Met Met Ser
             20                  25                  30

Lys Ser Leu His Val Leu Asp Glu Thr Leu Lys Asp Ile Ile Gly Asp
         35                  40                  45

His Val Gly Phe Pro Lys Cys Phe Lys Met Met Asp Met Gly Cys Ser
     50                  55                  60

Ser Gly Pro Asn Ala Leu Leu Val Met Ser Gly Ile Ile Asn Thr Ile
```

-continued

```
                65                  70                  75                  80
Glu Asp Leu Tyr Thr Glu Lys Asn Ile Asn Glu Leu Pro Glu Phe Glu
                    85                  90                  95

Val Phe Leu Asn Asp Leu Pro Asp Asn Phe Asn Asn Leu Phe Lys
            100                 105                 110

Leu Leu Ser His Glu Asn Gly Asn Cys Phe Val Tyr Gly Leu Pro Gly
            115                 120                 125

Ser Phe Tyr Gly Arg Leu Leu Pro Lys Lys Ser Leu His Phe Ala Tyr
        130                 135                 140

Ser Ser Tyr Ser Ile His Trp Leu Ser Gln Val Pro Glu Gly Leu Glu
145                 150                 155                 160

Asp Asn Asn Arg Gln Asn Ile Tyr Met Ala Thr Glu Ser Pro Pro Glu
                165                 170                 175

Val Tyr Lys Ala Tyr Ala Lys Gln Tyr Glu Arg Asp Phe Ser Thr Phe
            180                 185                 190

Leu Lys Leu Arg Gly Glu Glu Ile Val Pro Gly Gly Arg Met Val Leu
        195                 200                 205

Thr Phe Asn Gly Arg Ser Val Glu Asp Pro Ser Ser Lys Asp Asp Leu
    210                 215                 220

Ala Ile Phe Thr Leu Leu Ala Lys Thr Leu Val Asp Met Val Ala Glu
225                 230                 235                 240

Gly Leu Val Lys Met Asp Asp Leu Tyr Ser Phe Asn Ile Pro Ile Tyr
                245                 250                 255

Ser Pro Cys Thr Arg Glu Val Glu Ala Ala Ile Leu Ser Glu Gly Ser
            260                 265                 270

Phe Thr Leu Asp Arg Leu Glu Val Phe Arg Val Cys Trp Asp Ala Ser
        275                 280                 285

Asp Tyr Thr Asp Asp Asp Gln Gln Asp Pro Ser Ile Phe Gly Lys
    290                 295                 300

Gln Arg Ser Gly Lys Phe Val Ala Asp Cys Val Arg Ala Ile Thr Glu
305                 310                 315                 320

Pro Met Leu Ala Ser His Phe Gly Ser Thr Ile Met Asp Leu Leu Phe
                325                 330                 335

Gly Lys Tyr Ala Lys Lys Ile Val Glu His Leu Ser Val Glu Asn Ser
            340                 345                 350

Ser Tyr Phe Ser Ile Val Val Ser Leu Ser Arg Arg
        355                 360
```

<210> SEQ ID NO 3
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: At positions 12 and 18, n is a, c, g or t, or an unknown or other nucleotide.
<220> FEATURE:
<223> OTHER INFORMATION: Description of Artificial Sequence: oligonucleotide useful as a PCR primer; see Example 3.

<400> SEQUENCE: 3
garttygarg tnttyytnaa yga                                    23

<210> SEQ ID NO 4
<211> LENGTH: 20
<212> TYPE: DNA

```
<213> ORGANISM: Artificial Sequence
<220> FEATURE:
<223> OTHER INFORMATION: Description of Artificial Sequence:
      oligonucleotide useful as a primer in PCR; see
      Examples 4 and 7.
<220> FEATURE:
<221> NAME/KEY: misc_feature
<222> LOCATION: (1)..(20)
<223> OTHER INFORMATION: At positions 6, 12 and 15, n is a, c, g or t,
      or an unknown or other nucleotide.

<400> SEQUENCE: 4
acyaanccyt cngcnaccat                                                    20

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:
      oligonucleotide useful as a PCR primer; see
      Examples 4 and 7.

<400> SEQUENCE: 5
gtctagacat atgaaagtga tgaagaaac                                          29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence:
      oligonucleotide useful as a PCR primer; see
      Example 7.

<400> SEQUENCE: 6
tggatccttc atctcctact tagagaaac                                          29

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:
      oligonucleotide useful as a PCR primer; see
      Example 7.

<400> SEQUENCE: 7
ctctagacat atgaagaaac ttttgtg                                            27

<210> SEQ ID NO 8
<211> LENGTH: 359
<212> TYPE: PRT
<213> ORGANISM: Clarkia breweri

<400> SEQUENCE: 8

Met Asp Val Arg Gln Val Leu His Met Lys Gly Gly Ala Gly Glu Asn
  1               5                  10                  15

Ser Tyr Ala Met Asn Ser Phe Ile Gln Arg Gln Val Ile Ser Ile Thr
             20                  25                  30

Lys Pro Ile Thr Glu Ala Ala Ile Thr Ala Leu Tyr Ser Gly Asp Thr
         35                  40                  45

Val Thr Thr Arg Leu Ala Ile Ala Asp Leu Gly Cys Ser Ser Gly Pro
     50                  55                  60

Asn Ala Leu Phe Ala Val Thr Glu Leu Ile Lys Thr Val Glu Glu Leu
 65                  70                  75                  80
```

```
Arg Lys Lys Met Gly Arg Glu Asn Ser Pro Glu Tyr Gln Ile Phe Leu
                85                  90                  95
Asn Asp Leu Pro Gly Asn Asp Phe Asn Ala Ile Phe Arg Ser Leu Pro
            100                 105                 110
Ile Glu Asn Asp Val Asp Gly Val Cys Phe Ile Asn Gly Val Pro Gly
        115                 120                 125
Ser Phe Tyr Gly Arg Leu Phe Pro Arg Asn Thr Leu His Phe Ile His
    130                 135                 140
Ser Ser Tyr Ser Leu Met Trp Leu Ser Gln Val Pro Ile Gly Ile Glu
145                 150                 155                 160
Ser Asn Lys Gly Asn Ile Tyr Met Ala Asn Thr Cys Pro Gln Ser Val
                165                 170                 175
Leu Asn Ala Tyr Tyr Lys Gln Phe Gln Glu Asp His Ala Leu Phe Leu
            180                 185                 190
Arg Cys Arg Ala Gln Glu Val Val Pro Gly Gly Arg Met Val Leu Thr
        195                 200                 205
Ile Leu Gly Arg Arg Ser Glu Asp Arg Ala Ser Thr Glu Cys Cys Leu
    210                 215                 220
Ile Trp Gln Leu Leu Ala Met Ala Leu Asn Gln Met Val Ser Glu Gly
225                 230                 235                 240
Leu Ile Glu Glu Glu Lys Met Asp Lys Phe Asn Ile Pro Gln Tyr Thr
                245                 250                 255
Pro Ser Pro Thr Glu Val Glu Ala Glu Ile Leu Lys Glu Gly Ser Phe
            260                 265                 270
Leu Ile Asp His Ile Glu Ala Ser Glu Ile Tyr Trp Ser Ser Cys Thr
        275                 280                 285
Lys Asp Gly Asp Gly Gly Ser Val Glu Glu Gly Tyr Asn Val
    290                 295                 300
Ala Arg Cys Met Arg Ala Val Ala Glu Pro Leu Leu Asp His Phe
305                 310                 315                 320
Gly Glu Ala Ile Ile Glu Asp Val Phe His Arg Tyr Lys Leu Leu Ile
                325                 330                 335
Ile Glu Arg Met Ser Lys Glu Lys Thr Lys Phe Ile Asn Val Ile Val
            340                 345                 350
Ser Leu Ile Arg Lys Ser Asp
        355

<210> SEQ ID NO 9
<211> LENGTH: 371
<212> TYPE: PRT
<213> ORGANISM: Arabidopsis thaliana

<400> SEQUENCE: 9

Met Asp Lys Lys Asp Met Glu Arg Glu Phe Tyr Met Thr Gly Gly Asp
1               5                   10                  15
Gly Lys Thr Ser Tyr Ala Arg Asn Ser Ser Leu Gln Lys Lys Ala Ser
            20                  25                  30
Asp Thr Ala Lys His Ile Thr Leu Glu Thr Leu Gln Gln Leu Tyr Lys
        35                  40                  45
Glu Thr Arg Pro Lys Ser Leu Gly Ile Ala Asp Leu Gly Cys Ser Ser
    50                  55                  60
Gly Pro Asn Thr Leu Ser Thr Ile Thr Asp Phe Ile Lys Thr Val Gln
65                  70                  75                  80
Val Ala His His Arg Glu Ile Pro Ile Gln Pro Leu Pro Glu Phe Ser
```

-continued

```
            85                  90                  95

Ile Phe Leu Asn Asp Leu Pro Gly Asn Asp Phe Asn Phe Ile Phe Lys
                100                 105                 110

Ser Leu Pro Asp Phe His Ile Glu Leu Lys Arg Asp Asn Asn Asn Gly
            115                 120                 125

Asp Cys Pro Ser Val Phe Ile Ala Ala Tyr Pro Gly Ser Phe Tyr Gly
130                 135                 140

Arg Leu Phe Pro Glu Asn Thr Ile His Phe Val Tyr Ala Ser His Ser
145                 150                 155                 160

Leu His Trp Leu Ser Lys Val Pro Thr Ala Leu Tyr Asp Glu Gln Gly
                165                 170                 175

Lys Ser Ile Asn Lys Gly Cys Val Ser Ile Cys Ser Leu Ser Ser Glu
            180                 185                 190

Ala Val Ser Lys Ala Tyr Cys Ser Gln Phe Lys Glu Asp Phe Ser Ile
            195                 200                 205

Phe Leu Arg Cys Arg Ser Lys Glu Met Val Ser Ala Gly Arg Met Val
        210                 215                 220

Leu Ile Ile Leu Gly Arg Glu Gly Pro Asp His Val Asp Arg Gly Asn
225                 230                 235                 240

Ser Phe Phe Trp Glu Leu Leu Ser Arg Ser Ile Ala Asp Leu Val Ala
                245                 250                 255

Gln Gly Glu Thr Glu Glu Lys Leu Asp Ser Tyr Asp Met His Phe
            260                 265                 270

Tyr Ala Pro Ser Ala Asp Glu Ile Glu Gly Glu Val Asp Lys Glu Gly
            275                 280                 285

Ser Phe Glu Leu Glu Arg Leu Glu Met Leu Glu Val Lys Lys Asp Lys
        290                 295                 300

Gly Asn Thr Glu Gly Asp Ile Ser Tyr Gly Lys Ala Val Ala Lys Thr
305                 310                 315                 320

Val Arg Ala Val Gln Glu Ser Met Leu Val Gln His Phe Gly Glu Lys
                325                 330                 335

Ile Leu Asp Lys Leu Phe Asp Thr Tyr Cys Arg Met Val Asp Asp Glu
            340                 345                 350

Leu Ala Lys Glu Asp Ile Arg Pro Ile Thr Phe Val Val Val Leu Arg
            355                 360                 365

Lys Lys Leu
    370

<210> SEQ ID NO 10
<211> LENGTH: 359
<212> TYPE: PRT
<213> ORGANISM: Arabidopsis thaliana

<400> SEQUENCE: 10

Met Lys Gly Gly Thr Gly Asp His Ser Tyr Ala Thr Asn Ser His Tyr
1               5                   10                  15

Gln Arg Ser Val Phe Tyr Glu Ile Gln Pro Leu Val Ile Glu Asn Val
            20                  25                  30

Arg Glu Met Leu Leu Lys Asn Gly Phe Pro Gly Cys Ile Lys Val Ala
        35                  40                  45

Asp Leu Gly Cys Ser Thr Gly Gln Asn Thr Val Leu Ala Met Ser Ala
    50                  55                  60

Ile Ala Tyr Thr Ile Met Glu Ser Tyr Gln Gln Met Ser Lys Asn Pro
65                  70                  75                  80
```

-continued

```
Pro Glu Ile Asp Cys Tyr Leu Asn Asp Leu Pro Glu Asn Asp Phe Asn
            85                  90                  95

Thr Thr Phe Lys Leu Phe His Ser Phe Gln Glu Lys Leu Lys Pro Glu
           100                 105                110

Val Lys Gly Lys Trp Phe Val Ser Gly Val Pro Gly Ser Phe Tyr Ser
           115                 120                125

Arg Leu Phe Pro Arg Lys Ser Leu His Phe Val His Ser Ala Phe Ser
           130                 135             140

Ile His Trp Leu Ser Arg Ile Pro Asp Gly Leu Glu Ser Asn Thr Lys
145                 150                 155                 160

Ser Ile His Ile Lys Tyr Pro Tyr Pro Ser Asn Val Tyr Lys Ser Tyr
               165                 170                 175

Leu Asn Gln Phe Lys Ile Asp Phe Ser Leu Phe Leu Lys Met Arg Ser
               180                 185                 190

Glu Glu Val Val His Asn Gly His Met Val Leu Thr Phe Val Gly Arg
               195                 200                 205

Lys Val Ser Asp Thr Leu Ser Lys Asp Cys Phe Gln Val Trp Ser Leu
           210                 215                 220

Leu Ser Asp Cys Leu Leu Asp Leu Ala Ser Glu Gly Phe Val Asn Asp
225                 230                 235                 240

Ser Met Val Lys Ser Phe Asn Met Pro Phe Tyr Asn Pro Asn Glu Glu
               245                 250                 255

Glu Val Arg Glu Phe Ile Leu Lys Glu Gly Ser Phe Glu Ile Thr Lys
               260                 265                 270

Ile Glu Lys Phe Asp His Val Val Pro Tyr Lys Ile Asp Arg Glu Glu
               275                 280                 285

Glu Asp Glu Glu Gln Ser Leu Gln Leu Glu Ala Gly Ile Lys His Ala
           290                 295                 300

Ser Trp Ala Arg Cys Ile Thr Glu Pro Leu Leu Val Ala His Phe Gly
305                 310                 315                 320

Asp Ala Ile Ile Glu Pro Val Phe Asn Lys Tyr Ala His Tyr Met Ala
               325                 330                 335

Lys Tyr Leu Ser Val Ser Asn His Arg Arg Asn Met Thr Leu Val Ile
               340                 345                 350

Val Val Ser Leu Thr Arg Lys
           355
```

METHODS AND COMPOSITIONS FOR PRODUCTION OF FLORAL SCENT COMPOUNDS

CROSS-REFERENCE TO RELATED APPLICATIONS

The present application claims the benefit of U.S. Provisional Patent Application Ser. No. 60/152,393, filed on Sep. 3, 1999, which is hereby incorporated by reference in its entirety.

ACKNOWLEDGMENT OF FEDERAL RESEARCH SUPPORT

This invention was made with government support under grant number IBN-9904910 awarded by the National Science Foundation. The Government has certain rights in the invention. This invention was also made with support from Fred Cloeckner Foundation, Inc.

BACKGROUND OF THE INVENTION

The present invention relates generally to the field of floral scent production.

Floral scent is a key modulating factor in plant-insect interactions and plays a central role in successful pollination, and thus in fruit development, of many crop species. Flower fragrances vary widely among species in terms of the number, identity, and relative amounts of constituent volatile compounds (Knudsen and Tollsten, 1993, Knudsen et al., 1993). Closely related plant species, which rely on different insects for pollination, produce different odors (Henderson, 1986; Raguso and Pichersky, 1995). Often, characteristic floral odors are correlated with the type of pollinators. Species pollinated by bees and flies tend to have scents that are defined (by humans) as "sweet," whereas those pollinated by beetles have "musty," "spicy," or "fruity" odors (Dobson,1994).

Some volatile compounds found in floral scent also have important functions in vegetative processes. They may function as attractants to the natural predators of herbivores (Rose et al., 1996; Pare and Tumlinson, 1997) or as airborne signals that activate disease resistance via the expression of defense-related genes in the healthy tissues of infected plants and in neighboring plants (Farmer and Rayan, 1990; Shulaev et al., 1997; Seskar et al., 1998). They may also serve as repellents against herbivores (Levin, 1973; Rodriguez and Levin, 1976; Pellmyr et al, 1987; Gershenzon and Croteau, 1991).

Many volatile components of flowers have been identified; however, the mechanism of flower fragrance formation is not well understood. Recent investigations of floral scent production in *Clarkia breweri* are the first example of the isolation of enzymes and genes responsible for the biosynthesis of scent volatiles. The enzymes S-linalool synthase, S-adenosyl-L-methionine (SAM):(iso)eugenol O-methyl transferase, acetyl-coenzyme A:benzyl alcohol acetyltransferase, and S-adenosyl-L-methionine:salicylic acid carboxyl methyl transferase, which catalyze the formation of linalool, methyl(iso)eugenol, benzylacetate, and methyl salicylate, respectively, and their corresponding genes have been isolated and characterized (Dudareva et al., 1996; 1998a, b; Pichersky et al., 1994; 1995; Wang et al., 1997; Wang and Pichersky, 1998; Ross et al., 1999; reviewed in Dudareva and Pichersky, 2000). It has been shown that in *C. breweri*, flowers synthesize their scent compounds de novo in the tissues from which they are emitted, and that their emission levels, corresponding enzyme activities, and mRNA levels are all spatially and temporally correlated. In general, the expression of these genes is highest in petals just before anthesis and is restricted to the epidermal cell layer of floral tissues.

Although production of volatile scent compounds appears to be widespread in the plant kingdom, information about their de novo biosynthesis (as distinct from their possible release from glucosides; see Oka et al., 1999) and regulation of the genes involved is limited and based to date on the analysis of a single model system—moth-pollinated *C. breweri*. Whether similar molecular mechanisms are involved in regulation of floral scent production in other plant species is currently unclear. Several genes encoding flower pigment biosynthetic enzymes and also genes controlling flower development have been isolated from snapdragon (Coen et al., 1986; Sommer and Saedler, 1986; Coen and Meyerowitz, 1991; Irish and Yamamoto, 1995), but there is no information about enzymes and genes involved in the synthesis of flower scent compounds. There is thus a need for a better understanding of floral scent production, especially in snapdragon flowers which represent a very good model system. The present invention addresses this need.

SUMMARY OF THE INVENTION

A novel protein, S-adenosyl-L-methionine:benzoic acid carboxymethyltransferase, BAMT, that functions as an enzyme in the production of floral scent compounds, has been discovered. Accordingly, in a first aspect of the invention, purified BAMT proteins are provided.

In a second aspect of the invention, isolated nucleic acid molecules that encode BAMT proteins are provided. The nucleic acid molecules may be incorporated into a vector to form a recombinant nucleic acid molecule. Moreover, such recombinant nucleic acid molecules may be introduced into a host cell. Host cells, and transgenic plants, having the introduced nucleic acid nucleic acid molecules encoding a protein as described herein are specifically provided.

In a third aspect of the invention, a method of transforming a host cell is provided that includes introducing into a host cell a nucleic acid molecule encoding a protein described herein.

In fourth aspect of the invention, methods of expressing BAMT proteins are provided. The methods include transforming a host cell with a nucleotide sequence encoding a protein that functions in production of floral scent compounds as provided herein, and culturing the transformed host cells under conditions effective in achieving expression of BAMT proteins. The proteins may then be purified by conventional techniques.

It is an object of the invention to provide purified, functional BAMT proteins.

It is a further object of the invention to provide nucleotide sequences encoding functional BAMT proteins.

It is a further object of the invention to provide recombinant vectors that include nucleotide sequences encoding functional BAMT proteins.

It is yet another object of the invention to provide host cells containing introduced nucleotide sequences encoding functional BAMT proteins.

It is a further object of the invention to provide transgenic plants containing introduced nucleotide sequences encoding functional BAMT proteins.

These and other objects and advantages of the present invention will be apparent from the descriptions herein.

BRIEF DESCRIPTION OF THE FIGURES

FIG. 1A depicts emission of methyl benzoate during the life span of the flower, from mature flower buds one day before opening to 12 days after anthesis. Data are means ±SE (n=5). FIG. 1B depicts emission of methyl benzoate within a 24-hr period. Headspace collections were as described in Example 1. Black bars show emission, the curved line—photosynthetic photon flux.

FIGS. 3A–3B depict Antirrhinum flowers with a visiting bumblebee. In FIG. 3A, the bumblebee is in flight, approaching the flower. Only upper and lower petal lobes are facing the bee during landing. In FIG. 3B, a bumblebee is entering the snapdragon flower in the classic way described in Example 2.

FIG. 3C depicts a graph showing BAMT activity in different flower parts of 6-day-old snapdragon flower as described in Example 2. Values are the average of five independent measurements. pkat, Picomole of product per second.

FIG. 3D depicts a graph showing changes in BAMT activity during flower development as described in Example 2. Data are shown only for upper and lower petal lobes that contained BAMT activity.

FIG. 4 shows a comparison of the predicted amino acid sequence of Snapdragon BAMT protein (SEQ ID NO:2) with related proteins as described in Example 3. SAMT is SAM:salicylic acid carboxyl methyl transferase from *C. breweri* (SEQ ID NO:8) (GenBank accession number AF133053). Proteins with GenBank accession numbers Z997081 (SEQ ID NO:9) and AC0065281 (SEQ ID NO:10) correspond to two hypothetical proteins from Arabidopsis. Black boxes indicate conserved amino acid residues and dashes indicate gaps that have been inserted for optimal alignment. Sequences were aligned and displayed using the ClustalW and Boxshade 3.21 software programs (Human Genome Sequencing Center, Huston, Tex.).

FIG. 5A, analysis of methyl benzoate standard; FIG. 5B, analysis of the medium of *E. coli* cells expressing pET-T7 (11a) vector with no insert after induction with isopropyl β-D-thiogalactopyranoside; FIG. 5C, analysis of the medium (not supplemented with benzoic acid) of *E. coli* cells expressing snapdragon BAMT after induction with isopropyl β-D-thiogalactopyranoside; FIG. 5D, analysis of the medium (supplemented with 5 μg/ml benzoic acid as described in Example 4) of *E. coli* cells expressing snapdragon BAMT after induction with isopropyl β-D-thiogalactopyranoside. Toluene was added to all samples as an internal standard. Indole is produced by all *E. coli* cells (Dudareva et al., 1998a; Ross et al., 1999). Numbered peaks in FIGS. 5A, 5C and 5D represent mass-to-charge ratios of molecular ion and fragment ions of methyl benzoate.

In FIG. 6A, total RNA was isolated from young leaves, sepals, pistil, stamens, upper and lower petal lobes, and tubes of 6-day-old flower and 7 μg of total RNA was loaded in each lane as described in Example 5. The top gel represents the results of hybridization with a BAMT probe. The length of the BAMT mRNA was estimated at 1.6 kb by using RNA molecular markers in an adjacent lane. The blot was rehybridized with an 18S rDNA probe (bottom) to standardize samples. FIG. 6B, is an RNA gel blot hybridization with mRNA from upper and lower petal lobes at different stages of development. Each lane contained 3 μg of total RNA. The blots were rehybridized with an 18S rDNA probe (bottom) to standardize samples.

FIG. 8B, EIMS of derivatized authentic benzoic acid. Molecular weight of derivatized benzoic acid is 194; after ionization, the highest mass-to-charge ratio (m/z) is the loss of a $CH_3$ radical resulting in m/z of 179; FIG. 8C, EIMS of derivatized benzoic acid isolated from 2-day-old snapdragon petals. A peak corresponding to benzoic acid was collected after HPLC, derivatized and analyzed by GC-MS; In FIGS. 8B and 8C, numbered peaks are the mass-to-charge ratios of the fragment ions of the derivatized benzoic acid.

FIG. 9A, BAMT activity data are shown in FIG. 3D; the amount of BAMT protein is shown in FIG. 7B; FIG. 9B, the emitted amount of methyl benzoate is shown in FIG. 1A. Predicted production of methyl benzoate was calculated based on the equations 1 and 2 in Example 1. R=correlation coefficient.

FIG. 10A, DE 53; FIG. 10B, Phenyl Sepharose 6FF (low sub); and FIG. 10C, Mono-Q. The dotted lines represent the amount of protein in FIGS. 10A and 10B or absorbance at 280 nm in FIG. 10C, and the solid circles represent the BAMT activity expressed relative to the most active fraction (100%) in each chromatographic step. The dashed lines show salt gradients used during purification steps.

FIG. 13A, double-reciprocal plots of initial velocities with SAM varied in the presence of different concentrations of BA; Product inhibition: FIG. 13B, inhibition of methylation reaction by SAH with respect to SAM; the concentration of BA was fixed at 4 mM; FIG. 13C, inhibition of methylation reaction by SAH with respect to BA, the concentration of SAM was fixed at 150 μM.

DESCRIPTION OF THE PREFERRED EMBODIMENTS

Figure 1A:
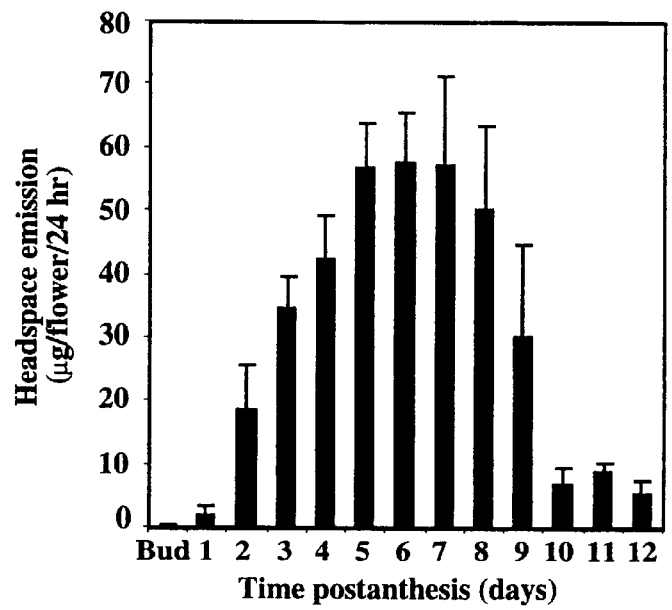
FIGS. 1A–1B depict emission of methyl benzoate from snapdragon flowers measured by headspace collection and gas chromatography—mass spectrometry (GC-MS) analysis as described in Example 1.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

A novel enzyme, S-adenosyl-L-methionine:benzoic acid carboxyl methyltransferase (BAMT), functioning in the production of floral scent compounds and including biosynthesis, or other production of floral scent compounds, has been identified in snapdragon flowers, *Antirrhinum majus*. Accordingly, the present invention provides purified BAMT proteins. The invention further provides isolated nucleic acid molecules that include nucleotide sequences encoding functional BAMT proteins. Recombinant nucleic acid molecules are also provided that include the novel BAMT nucleotide sequence. The nucleic acid molecules may be incorporated in a host cell and may be used to form a transgenic plant. In other aspects of the invention, methods of expressing functional BAMT protein and methods of transforming a host cell are also provided.

In a first aspect of the invention, purified BAMT proteins are provided that function in production of floral scent compounds. The BAMT proteins include enzymes that function in the synthesis of floral scent compounds, such as methyl benzoate. In preferred forms of the invention, the enzymes catalyze the transfer of a methyl group from a methyl group donor, such as S-adenosyl methionine (SAM), to benzoic acid to form methylbenzoate. The BAMT polypeptides are substantially pure (i.e., BAMT proteins are essentially free, e.g., at least about 95% free, from other proteins with which they naturally occur). In one preferred embodiment, the amino acid sequence of a BAMT protein, originally found in *Antirrhinum majus*, is set forth in SEQ ID NO:2, and includes amino acids 3–364 as well as the entire sequence shown in SEQ ID NO:2. The snapdragon model has several important advantages over the C. breweri system. With respect to snapdragons, there is a well-developed genetic map (Stubbe, 1966), a transposon gene cloning system (Martin et al, 1990), an available transformation protocol (Heidmann et al., 1998), and rhythmic emission (see below).

Although the invention is described with reference to *Antirrhinum majus* amino acid sequences, it is understood that the invention is not limited to the specific amino acid sequences set forth in SEQ ID NO:2. Skilled artisans will recognize that, through the process of mutation and/or evolution, polypeptides of different lengths and having differing constituents, e.g., with amino acid insertions, substitutions, deletions, and the like, may arise that are related to, or sufficiently similar to, a sequence set forth herein by virtue of amino acid sequence homology and advantageous functionality as described herein. The terms "BAMT protein" or "BAMT enzyme" are used to refer generally to proteins having the features described herein and a preferred example includes a polypeptide having the amino acid sequence of SEQ ID NO:2. Also included within this definition, and in the scope of the invention, are variants of the polypeptide which function in production of floral scent compounds, as described herein.

It is well known that plants of a wide variety of species commonly express and utilize homologous proteins, which include the insertions, substitutions and/or deletions discussed above, and yet which effectively provide similar function. For example, an amino acid sequence isolated from another species may differ to a certain degree from the sequence set forth in SEQ ID NO:2, and yet have similar functionality with respect to catalytic and regulatory function. Amino acid sequences comprising such variations are included within the scope of the present invention and are considered substantially or sufficiently similar to a reference amino acid sequence. Although not being limited by theory, it is believed that the identity between amino acid sequences that is necessary to maintain proper functionality is related to maintenance of the tertiary structure of the polypeptide such that specific interactive sequences will be properly located and will have the desired activity. Although it is not intended that the present invention be limited by any theory by which it achieves its advantageous result, it is contemplated that a polypeptide including these interactive sequences in proper spatial context will have good activity, even where alterations exist in other portions thereof In this regard, a BAMT protein variant is expected to be functionally similar to that set forth in SEQ ID NO:2, for example, if it includes amino acids which are conserved among a variety of species or if it includes non-conserved amino acids which exist at a given location in another species that expresses a functional BAMT protein.

Another manner in which similarity may exist between two amino acid sequences is where a given amino acid of one group (such as a non-polar amino acid, an uncharged polar amino acid, a charged polar acidic amino acid or a charged polar basic amino acid) is substituted with another amino acid from the same amino acid group. For example, it is known that the uncharged polar amino acid serine may commonly be substituted with the uncharged polar amino acid threonine in a polypeptide without substantially altering the functionality of the polypeptide. If one is unsure whether a given substitution will affect the functionality of the enzyme, then this may be determined without undue experimentation using synthetic techniques and screening assays known in the art.

The invention therefore also encompasses amino acid sequences similar to the amino acid sequences set forth herein that have at least about 50% identity thereto and function in production of floral scent compounds. Preferably, inventive amino acid sequences have at least about 70% identity, further preferably at least about 80% identity, and most preferably at least about 90% identity to these sequences.

Percent identity may be determined, for example, by comparing sequence information using the advanced BLAST computer program, version 2.1, available from the National Institutes of Health. The BLAST program is based on the alignment method of Karlin and Altschul, *Proc. Natl. Acad. Sci. USA* 87:2264–68 (1990) and as discussed in Altschul, et al., *J. Mol. Biol.* 215:403–10 (1990); Karlin and Altschul, *Proc. Natl. Acad. Sci. USA* 90:5873–7 (1993); and Altschul et al. (1997) *Nucleic Acids Res.* 25:3389–3402. Briefly, the BLAST program defines identity as the number of identical aligned symbols (i.e., nucleotides or amino acids), divided by the total number of symbols in the shorter of the two sequences. The program may be used to determine percent identity over the entire length of the proteins being compared. Preferred default parameters for the BLAST program, blastp, include: (1) description of 100; (2) Karlin-Altschul parameter λ=0.32; (3) Karlin-Altschul parameter K=0.136; (4) gap penalties: Existence 11, Extension 1; (5) H value=0.399; and (6) scores for matched and mismatched amino acids found in the BLOSUM62 matrix as described in Henikoff, S. and Henikoff, J. G. (1992) *Proc. Natl. Acad. Sci. USA* 89:10915–10919;Pearson, W. R. (1995) *Prot. Sci.* 4:1145–1160; and Henikoff, S. and Henikoff, J. G. (1993) *Proteins* 17:49–61. The program also uses an SEG filter to mask-off segments of the query sequence as determined by the SEG program of Wootton and Federhen (1993) *Computers and Chemistry* 17:149–163.

In another aspect of the invention, isolated nucleic acid molecules, originally isolated from *Antirrhinum majus*, are provided that encode a BAMT protein that functions in production of floral scent compounds. The nucleotide sequence is set forth in SEQ ID NO:1. It is preferred that the nucleotide sequence includes nucleotides spanning the coding sequence, such as nucleotides 19 to 1110 or 1113 in SEQ ID NO:1. Moreover, as discussed in Example 7, in other forms of the invention the nucleotide sequence includes nucleotides spanning nucleotide 28 to 1110 or 1113 of SEQ ID NO:1. It is not intended that the present invention be limited to these exemplary nucleotide sequences, but include sequences having substantial similarity thereto and sequences which encode variant forms of functional BAMT protein as discussed above and as further discussed below.

The term "isolated nucleic acid," as used herein, is intended to refer to nucleic acid which is not in its native environment. For example, the nucleic acid is separated from other contaminants that naturally accompany it, such as proteins, lipids and other nucleic acid sequences. The term includes nucleic acid which has been removed or purified from its naturally-occurring environment or clone library, and further includes recombinant or cloned nucleic acid isolates and chemically synthesized nucleic acid.

The term "nucleotide sequence," as used herein, is intended to refer to a natural or synthetic linear and sequential array of nucleotides and/or nucleosides, including deoxyribonucleic acid (DNA) and ribonucleic acid (RNA), and derivatives thereof. The terms "encoding" and "coding" refer to the process by which a nucleotide sequence, through the mechanisms of transcription and translation, provides the information to a cell from which a series of amino acids can be assembled into a specific amino acid sequence to produce a functional polypeptide, such as, for example, an active enzyme or other protein that has a specific function. The process of encoding a specific amino acid sequence may involve DNA sequences having one or more base changes (i.e., insertions, deletions, substitutions) that do not cause a change in the encoded amino acid, or which involve base changes which may alter one or more amino acids, but do not eliminate the functional properties of the polypeptide encoded by the DNA sequence.

It is therefore understood that the invention encompasses more than the specific exemplary nucleotide sequence of BAMT. For example, nucleic acid sequences encoding variant amino acid sequences, as discussed above, are within the scope of the invention. Modifications to a sequence, such as deletions, insertions, or substitutions in the sequence, which produce "silent" changes that do not substantially affect the functional properties of the resulting polypeptide molecule are expressly contemplated by the present invention. For example, it is understood that alterations in a nucleotide sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, may also be expected to produce a biologically equivalent product.

Nucleotide changes which result in alteration of the N-terminal and C-terminal portions of the encoded polypeptide molecule would also not generally be expected to alter the activity of the polypeptide. In some cases, it may in fact be desirable to make mutations in the sequence in order to study the effect of alteration on the biological activity of the polypeptide. Each of the proposed modifications is well within the routine skill in the art.

In one preferred embodiment, the nucleotide sequence has substantial similarity to the sequence set forth in SEQ ID NO:1, preferably the sequence spanning nucleotides 19 to 1110 or 1113 in SEQ ID NO:1, and variants described herein including nucleotides 28 to 1110 or 1113 in SEQ ID NO:1. The term "substantial similarity" is used herein with respect to a nucleotide sequence to designate that the nucleotide sequence has a sequence sufficiently similar to a reference nucleotide sequence that it will hybridize therewith under moderately stringent conditions. This method of determining similarity is well known in the art to which the invention pertains. Briefly, moderately stringent conditions are defined in Sambrook et al., *Molecular Cloning: A Laboratory Manual,* 2nd ed. Vol. 1, pp. 101–104, Cold Spring Harbor Laboratory Press (1989) as including the use of a prewashing solution of 5×SSC (a sodium chloride/sodium citrate solution), 0.5% sodium dodecyl sulfate (SDS), 1.0 mM ethylene diaminetetraacetic acid (EDTA) (pH 8.0) and hybridization and washing conditions of 55° C., 5×SSC. A further requirement of the inventive polynucleotide is that it must encode a polypeptide having similar functionality to the BAMT protein described herein, i.e., function in production of floral scent compounds.

In yet another embodiment, nucleotide sequences having selected percent identities to specified regions of the nucleotide sequence set forth in SEQ ID NO:1 are provided. In one preferred form, nucleotide sequences are provided that have at least about 30% identity, preferably at least about 50% identity, more preferably at least about 70% identity, further preferably at least about 80% identity, and most preferably at least about 90% identity, to a nucleotide sequence of substantial length within the nucleotide sequence set forth in SEQ ID NO:1. For example, such length may be 100, 200, 300, 400 or 500 nucleotides, or may be the entire sequence in SEQ ID NO:1. A further requirement is that the nucleotide sequence set forth in SEQ ID NO:1 encodes a protein that functions in production of floral scent compounds as described herein. The percent identity may be determined, for example, by comparing sequence information using the advanced BLAST computer program, version 2.1, as described above with reference to amino acid identity. Preferred default parameters for blastn include: (1) Karlin-Altschul parameter λ=1.37 (gapped and ungapped); (2) Karlin-Altschul parameter K=0.711 (gapped and ungapped); (3) H value=1.31 (gapped and zero for ungapped); (4) gap penalties: Existence 5, Extension 2; and (5) scores for matched and mismatched nucleotides found in the blastn matrix as described in Altschul, S. F. et al. (1997) *Nucleic Acids Res.* 25:3389–3402 and Zhang, J. (1997) *Genome Res.* 7:649–656.

A suitable DNA sequence may be obtained by cloning techniques using cDNA libraries. For example, *Antirrhinum majus* cDNA libraries may be constructed using standard methods known in the art. Suitable nucleotide sequences may be isolated from DNA libraries obtained from a wide variety of species by means of nucleic acid hybridization or polymerase chain reaction (PCR) procedures, using as probes or primers nucleotide sequences selected in accordance with the invention, such as those set forth in SEQ ID NO:1, nucleotide sequences having substantial similarity thereto, or portions thereof.

Alternately, a suitable sequence may be made by techniques which are well known in the art. For example, nucleic acid sequences encoding a functional BAMT protein may be constructed by recombinant DNA technology, for example, by cutting or splicing nucleic acids using restriction enzymes and DNA ligase. Furthermore, nucleic acid sequences may be constructed using chemical synthesis, such as solid-phase phosphoramidate technology. PCR may be used to increase the quantity of nucleic acid produced. Moreover, if the particular nucleic acid sequence is of a length which makes chemical synthesis of the entire length impractical, the sequence may be broken up into smaller segments which may be synthesized and ligated together to form the entire desired sequence by methods known in the art.

In another aspect of the invention, BAMT polypeptides functioning in production of floral scent compounds and having the amino acid sequences encoded by nucleotide sequences having substantial similarity to the nucleotide sequences described above are also provided.

In a further aspect of the invention, recombinant nucleic acid molecules, or recombinant vectors, are provided. In one embodiment, the nucleic acid molecules include a nucleotide sequence encoding a functional BAMT protein. The nucleotide sequence may have the selected percent identities, or substantial similarity, both as defined above, to the nuclebtide sequence set forth in SEQ ID NO:1, preferably the sequence spanning nucleotides 19 to 1110 or 1113 in SEQ ID NO:1, or portions thereof described herein. The protein produced has the amino acid sequence set forth in SEQ ID NO:2, or variants thereof as described above.

Recombinant vectors may be constructed by incorporating the desired nucleotide sequence within a vector according to methods well known to the skilled artisan and as described, for example, in Sambrook et al. (Eds.), *Molecular Cloning: A Laboratory Manual,* 2nd ed., Cold Spring Harbor Laboratory Press, Cold Spring Harbor, N.Y. (1989). A wide variety of vectors are known that have use in the invention. For example, various plasmid and phage vectors are known that are ideally suited for use in the invention. For example, λZAPII. pB[SK$^+$], TA-vector and pET-7 may be used in the invention. In preferred embodiments, the vector may be a T-DNA vector. Representative T-DNA vector systems are discussed in the following publications: An et al., (1986) EMBO J. 4:277; Herrera-Estrella et al., (1983) EMBO J. 2:987; Herrera-Estrella et al., (1985) in *Plant Genetic Engineering,* New York: Cambridge University Press, p. 63.

In one embodiment, the desired recombinant vector may be constructed by ligating DNA linker sequences to the 5' and 3' ends of the desired nucleotide insert, cleaving the insert with a restriction enzyme that specifically recognizes sequences present in the linker sequences and the desired vector, cleaving the vector with the same restriction enzyme, mixing the cleaved vector with the cleaved insert and using DNA ligase to incorporate the insert into the vector as known in the art.

The vectors may include other nucleotide sequences, such as those encoding selectable markers, including those for antibiotic resistance or color selection. The vectors also preferably include a promoter nucleotide sequence. The desired nucleic acid insert is preferably operably linked to the promoter. A nucleic acid is "operably linked" to another nucleic acid sequence, such as a promoter sequence, when it is placed in a specific functional relationship with the other nucleic acid sequence. The functional relationship between a promoter and a desired nucleic acid insert typically involves the nucleic acid and the promoter sequences being contiguous such that transcription of the nucleic acid sequence will be facilitated. Two nucleic acid sequences are further said to be operably linked if the nature of the linkage between the two sequences does not (1) result in the introduction of a frame-shift-mutation; (2) interfere with the ability of the promoter region sequence to direct the transcription of the desired nucleotide sequence, or (3) interfere with the ability of the desired nucleotide sequence to be transcribed by the promoter sequence region. Typically, the promoter element is generally upstream (i.e., at the 5' end) of the nucleic acid insert coding sequence.

A wide variety of promoters are known in the art, including cell-specific promoters, inducible promoters, and constitutive promoters. The promoters may be of viral, bacterial or eukaryotic origin, including those from plants and plant viruses. Suitable promoters include those of viral origin, such as a cauliflower mosaic virus promoter (CaMV), including CaMV 35S or 19S, a figwort mosaic virus promoter (FMV 35S), or the coat protein promoter of tobacco mosaic virus (TMV). The promoter may further be, for example, a promoter for the small subunit of ribulose-1,3-diphosphate carboxylase. Promoters of bacterial origin include the octopine synthase promoter, the nopaline synthase promoter and other promoters derived from native Ti plasmids as discussed in Herrera-Estrella et al., *Nature* 303:209–213 (1983).

The promoters may further be selected such that they require activation by activating elements known in the art, so that production of the protein encoded by the nucleic acid sequence insert may be regulated as desired. Preferred promoters are foreign promoters. A "foreign promoter" is defined herein to mean a promoter other than the native, or natural, promoter which promotes transcription of a length of DNA.

The vectors may further include other regulatory elements, such as enhancer sequences, which cooperate with the promoter to achieve transcription of the nucleic acid insert coding sequence. By "enhancer" is meant nucleotide sequence elements which can stimulate promoter activity in a cell, such as a bacterial or eukaryotic host cell.

Moreover, the vectors may include another nucleotide sequence insert that encodes a protein that may aid in purification of the desired protein encoded by the desired nucleotide sequence. The additional nucleotide sequence is positioned in the vector such that a fusion, or chimeric, protein is obtained. For example, a BAMT protein may be produced having at its C-terminal end linker amino acids, as known in the art, joined to the other protein. For example, a protein described herein may be produced having at its C-terminal end several histidine molecules joined to the protein. Therefore, the additional nucleotide sequence may include, for example, the nucleotide sequence encoding multiple histidines. The protein may be isolated on a nickel chromatography column, which will bind the histidine in the protein being purified. After purification procedures known to the skilled artisan, the additional amino acid sequence may be cleaved with an appropriate enzyme, such as a protease. The BAMT protein may then be isolated from the other proteins, or fragments thereof, by methods known in the art.

The inventive recombinant vectors may be used to transform a host cell. Accordingly, methods of transforming a host cell as described herein are provided that include introducing into the host cell a nucleic acid molecule having a nucleotide sequence as described herein, such as one, for example, that encodes a protein as described herein that functions in production of floral scent compounds. Methods of transforming host cells, including plant cells, are well known in the art, and may be found in references such as Sambrook et al. (Eds.), *Molecular Cloning: A Laboratory Manual*, 2nd ed., Cold Spring Harbor Laboratory Press, Cold Spring Harbor, N.Y. (1989) and *Current Protocols in Molecular Biology*, John Wiley and Sons, Ausubel et al. (Ed.) (1988). Plant gene transfer techniques may also be found in references including Fromm et al., (1985) *Proc. Natl. Acad. Sci. USA*, 82:5824–5828 (lipofection); Crossway et al., (1986) *Mol. Gen. Genet.* 202:179 (microinjection); Hooykaas-Van Slogtern et al., (1984) *Nature* 311:763–764)(T-DNA mediated transformation of monocots); Rogers et al., (1986) *Methods Enzymol.* 118:627–641 (T-DNA mediated transformation of dicots); Bevan et al., (1982) *Ann. Rev. Genet.* 16:357–384) (T-DNA mediated transformation of dicots); Klein et al., (1988) *Proc. Natl. Acad. Sci USA* 85:4305–4309 (microprojectile bombardment); and Fromm et al., *Nature* (1986) 319:791–793 (electroporation). Once the desired nucleic acid has been introduced into the host cell, the host cell may produce the inventive BAMT protein, or variants thereof, as described above. Accordingly, in yet another aspect of the invention, a host cell is provided that includes the inventive recombinant vectors described above.

A wide variety of host cells may be used in the invention, including prokaryotic and eukaryotic host cells. Bacterial host cells such as *Escherichia coli*, HB 101, XL-1 blue and BL21(DE) may be advantageously used in the present invention. Typical eukaryotic host cells include *Agrobacterium tumefaciens* LBA 4404 and other transformable eukaryotic cells, including plant cells, such as, for example, plant cells from flowering plants as known in the art. In a further aspect of the invention, the host cells may be cultured as known in the art to produce a transgenic plant.

In yet another aspect of the invention, methods of producing functional BAMT proteins as described above are provided. In one embodiment, the method includes providing a nucleotide sequence described above, or variants thereof, that encodes a functional BAMT protein that functions in production of floral scent compounds, and introducing the nucleotide sequence into a host cell, as described above. The desired nucleotide sequence may be advantageously incorporated into a vector to form a recombinant vector. The recombinant vector may then be introduced into a host cell according to known procedures in the art. Such host cells are then cultured under conditions, well known to the skilled artisan, effective to achieve expression of the BAMT polypeptide. The BAMT polypeptide may then be purified using conventional techniques.

Reference will now be made to specific examples illustrating the invention described above. It is to be understood that the examples are provided to illustrate preferred embodiments and that no limitation to the scope of the invention is intended thereby.

EXAMPLE 1

Detection of Volatiles Emitted by Intact Flowers and Temporal and Rhythmic Variations in Emission of the Major Component, Methyl Benzoate Plant Material, Headspace Collection, and Gas Chromatography—Mass Spectrometry Analysis Seeds of 37 different Antirrhinum cultivars were kindly provided by Ball Seed Co., (West Chicago, Ill.). Plants were grown under standard greenhouse conditions. Volatiles emitted from snapdragon flowers were determined by headspace analysis as described previously (Raguso and Pellmyr, 1998; Raguso and Pichersky, 1995). Briefly, individual flowers attached to the plant were enclosed in a polyvinylacetate bag (Reynolds, Inc,) and purified air was pumped over the flower at a flow rate of 250 ml/min. Collection of floral scent compounds proceeded for 24 hours under greenhouse conditions. Existing volatiles were adsorbed on a Porapak Q (80–100 mesh size) cartridge (Alltech Inc.), eluted from the cartridge with 3 ml of hexane and concentrated to 75 $\mu$l. Trapped floral scent compounds were analyzed by gas chromatography—mass spectrometry (GC-MS) with a FinniganMAT GCQ instrument (Thermoquest, San Jose, Calif.) (injector temperature 230° C., injector volume 1 $\mu$L, and split ratio 50:1) using a DB-1 nonpolar capillary column (30 m×0.25 mm internal diameter; 0.25 $\mu$m film thickness). Ionization energy was set at 70 eV(electron volts). Column temperature programming was 50° C. for 1 min, with heating to 240° C. at a rate of 10° C./min. The mass spectrometer was scanned from 41–400 atomic mass units. Simultaneous collections of ambient volatiles were used as controls. Components were first identified through a computer database containing several thousand mass spectra and confirmed by comparison of retention times and mass spectra of authentic standards.

Estimation of Predicted Emission of Methyl Benzoate

Predicted production of methyl benzoate was calculated based on the Michaelis-Menten equations 1 and 2.

$$V_{predicted} = V_{\max} \frac{[S_{BA}]}{[S_{BA}] + K_m} \quad (1)$$

$V_{max}$ is maximal rate, $[S_{BA}]$ is benzoic acid concentration in petal tissue, $K_m$ is Michaelis constant of plant BAMT protein for benzoic acid, which is 1 mM (Murfitt, et al., 2000). $[S_{BA}]$ in petal tissue was calculated based on the amount of benzoic acid obtained experimentally (data from FIG. 8A) assuming that it is produced in cytoplasm and the volume of cytoplasm is 80 μL/g fresh weight (Winter et al., 1993).

$$V_{max} = V\frac{(S_o + K_m)}{S_o} = \frac{3}{2}V \qquad (2)$$

V is experimentally obtained activity of BAMT in upper and lower petal lobes during flower development (data from FIG. 3D), [$S_o$], concentration of benzoic acid in the enzymatic assays, 2 mM in our assay; $K_m$ of plant BAMT protein for benzoic acid, 1 mM.

Results

Headspace analysis in combination with gas chromatography and mass spectrometry of volatiles emitted from flowers of 37 different Antirrhinum cultivars revealed that snapdragon flower scent is dominated by myrcene, trans-β ocimene, and methyl benzoate. Methyl benzoate is the most abundant scent compound detected in the majority of snapdragon varieties. In these experiments, headspace compounds were collected from a single inflorescence with 8 to 12 flowers at 24-hr intervals. No correlation was found between the fragrance composition and different flower color. The highest level of methyl benzoate emission was found in the Maryland True Pink cultivar, where it comprises about 60% of the total volatiles as seen in Table 1 below. This cultivar was used for further investigations.

TABLE 1

Major volatile compounds identified from Maryland True Pink Snapdragon flowers

| Compound | Volatile Production[a] (μg/flower/24 hr) | Relative Amount (%)[b] |
|---|---|---|
| Myrcene | 7.7 ± 2.1 | 8.1 |
| Trans-β-ocimene | 26.0 ± 5.9 | 27.4 |
| Methyl benzoate | 56.5 ± 7.3 | 59.5 |

[a]Production of volatile compounds is shown for 5-day-old flowers.
[b]Minor volatile compounds comprise above 5% of total volatile production.

To determine variations in emission of methyl benzoate during the life span of flower development, time course headspace collections were conducted from single, living flowers at 24 hr intervals. Unopened flowers (buds) emitted no methyl benzoate (FIG. 1A). Emission of methyl benzoate began at anthesis, but at a very low level (1.8 μg per flower for 24 hr), reached a peak between days 5 to 8, and declined thereafter. Emission level at peak time was 56.5 μg per flower for a 24 hr period.

Figure 1B:
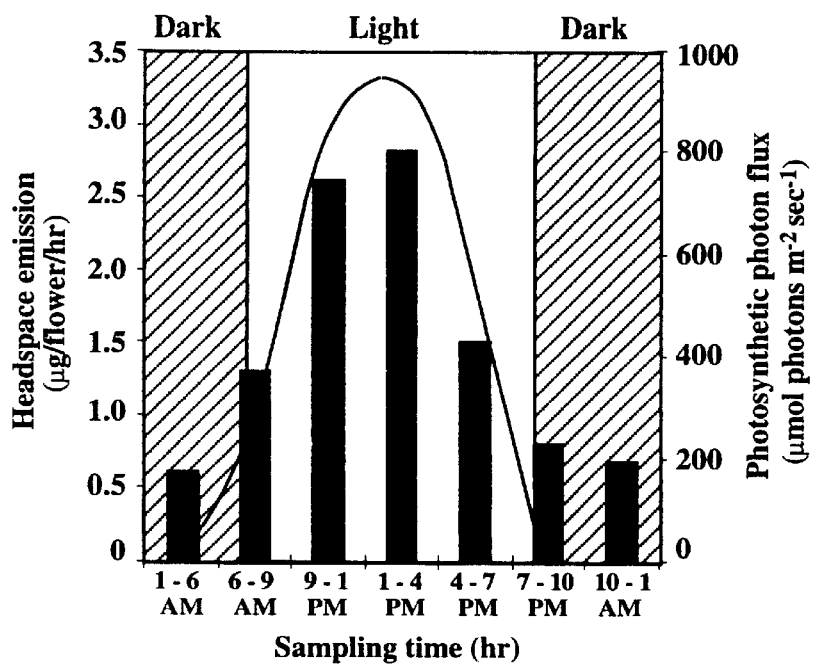

To determine variations in methyl benzoate emission during a 24 hr period, volatile compounds were collected from a 3-day-old flower during a 12 hr light period and a 12 hr dark period. These results revealed that snapdragon flowers produce methyl benzoate in a rhythmical, diurnal manner. Floral odor collected during the daytime contained four times more methyl benzoate per flower than during the night. Headspace collections were also performed at 3 hr intervals during the light period and 6-hr intervals at night to check for possible fluctuations in methyl benzoate emission during the light period (FIG. 1B). The emission of methyl benzoate was not stable during daytime: it peaks between 9 a.m. to 4 p.m. Maximum emission of methyl benzoate correlated with the light intensity in the greenhouse (FIG. 1B).

EXAMPLE 2

Analysis of BAMT Activity in Floral Tissues and at Different Stages of Flower Development BAMT Enzyme Assays and Product Analysis Crude protein extracts were prepared by homogenizing freshly excised flower parts in a chilled glass homogenizer in the presence of ice-cold extraction buffer (5:1 [v/w] buffer/tissue) containing 50 mM Bis-Tris-HCl, pH 6.9, 10 mM β-mercaptoethanol, 5 mM $Na_2S_2O_5$, 1% (w/v) polyvinylpyrrolidone (PVP-40), 1 mM phenylmethylsulfonyl fluoride, and 10% (v/v) glycerol. The slurry was centrifuged for 10 min to produce a supernatant that contained enzyme activity. For each time point, flower parts from at least five flowers from different plants were combined. Total soluble proteins were determined by the Bradford method (Bradford, 1976) using Bio-Rad protein reagent (Bio-Rad Laboratories, Hercules, Calif.) and BSA as a standard.

Enzyme activity was determined by measuring transfer of the $^{14}C$-labeled methyl group of SAM to the carboxyl group of benzoic acid. The standard reaction mixture (100 μL) included 20 μL of crude extract (25–40 μg of protein), 100 μM of S-adenosyl-L-methionine (SAM; containing 0.1 μCi) in assay buffer (50 mM Tris-HCl pH 7.5, and 3 mM 2-mercaptoethanol), containing 2 mM benzoic acid and 0.5 mM EDTA. After incubation for 30 min at 20° C., the radioactively-labeled methylated product was extracted by the addition of 100 μL hexane, and 50 μL of the organic phase was counted in a liquid scintillation counter (model LS 6800, Beckman, Fullerton, Calif.). The raw data (counts per minute) were converted to picokatals (picomoles of product produced per second) based on the specific activity of the substrate and efficiency of counting. Controls included assays with boiled protein extracts and without substrate, and background radioactivity produced in such assays was subtracted from all of the results.

Product verification was performed by thin-layer chromatography (TLC) as previously described (Wang et al., 1997) and by GC-MS. For the GC-MS analysis, the enzymatic reaction was scaled up to 1 mL final volume and contained 1 mM of nonradioactive SAM (Sigma). The reaction was carried out for 1 hr, and product was extracted with 1 mL of hexane, concentrated, and injected into the gas chromatograph—mass spectrometer.

Results

Figure 2:
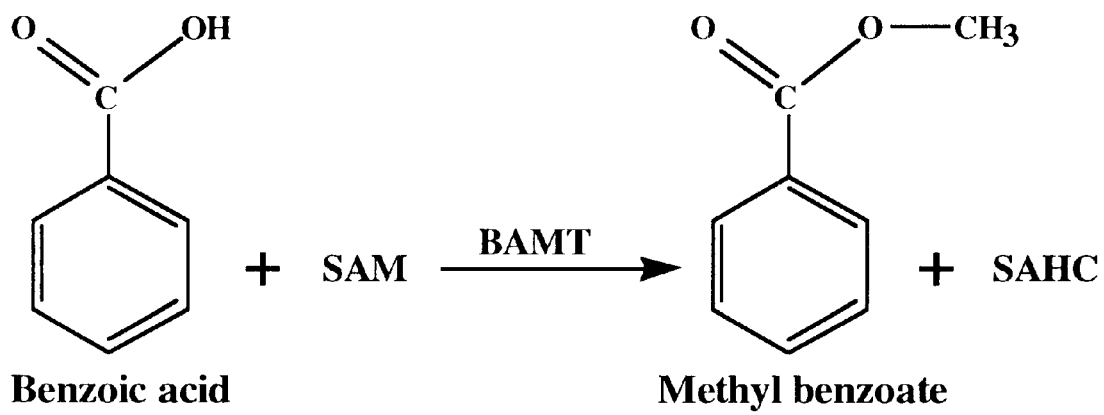
FIG. 2 depicts a schematic of the reaction catalyzed by BAMT. SAM is a donor of methyl group; SAHC, S-adenosyl-L-homocysteine.

Although methyl benzoate has been reported in the floral scent of more than 30 different species (Knudsen et al., 1993), the immediate biochemical step leading to its synthesis has not previously been elucidated. However, it appeared likely that methyl benzoate could be synthesized by enzymatic methylation of benzoic acid with SAM as the methyl group donor, in an analogous reaction to the synthesis of methyl salicylate from SAM and salicylic acid (Dudareva et al., 1998b). Therefore, an enzymatic assay was devised to test for benzoic acid carboxyl methyl transferase (BAMT) activity using nonradioactive benzoic acid and $^{14}C$-SAM as the methyl donor (FIG. 2).

Using this assay, BAMT activity was analyzed in crude extracts from different parts of snapdragon flowers and at different stages of flower development. The range was from just before anthesis, when mature flower buds appear, to 12 days after anthesis. Antirrhinum flowers are zygomorphic and contain five small sepals and five petals fused at the base into a tube, which divides distally into the upper and lower lobes. The two upper and three lower lobes close the mouth of the corolla tube (Coen and Meyerowitz, 1991) (FIG. 3A and 3B). Crude extracts were prepared from different flower organs and also from different regions of the corolla (the upper petal lobes, the lower petal lobes, and the tube) of 6-day-old flowers and tested for BAMT activity.

The majority of BAMT activity was found in the upper and lower lobes, with much less activity found in the tube and anthers (FIG. 3C). The values of 120, 130, and 200 mg were used for the total weight of the upper and lower lobes and the tube, respectively. Protein concentrations were 1.45, 1.83, and 0.72 mg/mL for the upper, lower lobes, and the tube, respectively, and can be used to calculate specific activities per milligram of protein. BAMT activity, calculated per milligram fresh weight of tissue, was about 10-fold higher in lower and upper lobes than in the tube (4.07, 2.8, and 0.37 pkat per mg fresh weight, respectively). None of the remaining floral organs (pistils, sepals, and ovaries) or leaves was found to contain BAMT activity. These results suggest that the main sites of methyl benzoate synthesis are the upper and lower petal lobes, which make almost equal contributions to the whole-flower fragrance.

In FIG. 3B, a bee enters the snapdragon flower in the classic way: the bee opens the mouth of the corolla tube, and only upper and lower lobes of the petals come in contact with the bee's body. In this way, a bee can be perfumed by floral scent produced only in upper and lower petal lobes. FIGS. 3A and 3B were donated by Iris Heidmann from the Max-Planck-lnstitut für Züchtungsforschung, Cologne, Germany.

In this study, it has also been determined that the level of BAMT activity in petals is developmentally regulated. The total BAMT activity gradually increased during the first 5 days after anthesis, remained relatively stable during the next 5 days, and decreased afterward (FIG. 3D). For each time point in FIG. 3D, enzyme assays were run in duplicate on at least five independent crude extract preparations and the standard deviations were obtained. No detectable BAMT activity was found in flower buds 1 day before the opening of the flower.

EXAMPLE 3

Isolation and Characterization of BAMT cDNA Clones

Enzyme Purification and Protein Sequencing

The enzyme activity was purified from upper and lower petal lobes of 5- to 10-day-old snapdragon flowers in a series of chromatographic steps involving a DEAE anion exchange column (DE53, Whatman International, Maidstone, England), phenyl Sepharose 6FF (low sub, level of phenyl substitution 20 µmole per ml gel) column (Pharmacia Biotech, Piscataway, N.J.), and another anion exchange column, MonoQ, on Pharmacia's fast-performance liquid chromatography system. A complete description of the purification protocol is described in Example 7.

Sequence analysis was performed with peptides produced by lysyl endopeptidase (Wako BioProducts, Wako Chemicals, Richmond, Va.) cleavage of purified BAMT protein. The digestion products were separated on a narrow-bore HPLC, using a C18 (21×250 mm) reverse phase column, and the amino acid sequences from six internal regions were determined in a protein sequencer (Procise, model 491, Applied Biosystems, Foster City, Calif.) by using standard protocols.

cDNA Library Construction

Total RNA was isolated from upper and lower petal lobes of 1- to 5-day-old snapdragon flowers by a slightly modified guanidium-chloride method, as described by Herdenberger et al. (1990). Poly(A) mRNA was isolated from total RNA using the poly-A-Ttract mRNA Isolation Systems (Promega, Madison, Wis.). A cDNA synthesis was performed according to the cDNA Synthesis Kit (Pharmacia Biotech, Piscataway, N.J.). A cDNA library was constructed in the Lambda-ZAP II vector (Stratagene, La Jolla, Calif.) according to company protocol. The titer of the unamplified library was $1.1 \times 10^6$.

Isolation and Characterization of cDNA Clones

For polymerase chain reaction (PCR) amplification of fragments of BAMT cDNA, several pairs of degenerate primers were synthesized based on the peptide sequences. PCR experiments were performed as previously described using a snapdragon petal-specific cDNA library as the target (Dudareva et al., 1996, 1998a). PCR experiments using the sense 23-mer oligonucleotide 5'-GARTTYGARGTNTTYYTNAAYGA-3' (wherein R is a purine, such as A or G; Y is a pyrimidine such as C or T; and N may be either A, C, G, T or an unknown or other nucleotide), shown in SEQ ID NO:3 (nucleotides 298–320 in SEQ ID NO:1 when, from 5' to 3', R=A, Y=T, R=G, N=T, Y=T, Y=C, N=G and Y=C), for amino acid sequence EFE-VFLND (positions 94 to 101 from the N terminus of SEQ ID NO:2), and the antisense 20-mer 5'-ACYAANCCYTCNGCNACCAT-3' (wherein Y and N are as defined above for SEQ ID NO:3), shown in SEQ ID NO:4 (sequence to target nucleotides 727–747 of SEQ ID NO:1 for PCR wherein the design was based upon the experimentally obtained protein sequence and wherein N and Y are as defined above for SEQ ID NO:3), for amino acid sequence MVAEGLV (positions 237 to 243 from the N terminus in SEQ ID NO:2), gave a product of 440 nucleotides. The amplified fragment was in turn used to screen the same cDNA library. Several cDNA clones, all containing the same open reading frame, were isolated and sequenced. The sequence of the longest clone was completely determined on both strands. The GenBank accession number of this sequence is AF198492.

Results

The BAMT protein was successively purified from 5- to 1 0-day-old upper and lower petal lobes (floral tissue with the highest BAMT specific activity) using a DE53 anion exchange, phenyl Sepharose 6FF (low sub, level of phenyl substitution 20 µmole per ml gel), and MonoQ chromatography. After the MonoQ chromatography step, the fraction with the highest BAMT activity contained one major protein with apparent molecular mass of 49 kD on a SDS-polyacrylamide gel. This fraction was also tested with several other naturally occurring substrates such as salicylic acid and trans-cinnamic acid and their derivatives (3-hydroxybenzoic acid, 4-hydroxybenzoic acid, benzyl alcohol, and 2-coumaric, 3-coumaric, and 4-coumaric acids). When these additional compounds were added, no activity was detected.

Sequencing of the N-terminus of the 49-kD protein was unsuccessful due to a blocked N terminus. Therefore, we subjected the purified BAMT protein to lysyl endopeptidase cleavage, and the amino acid sequences from six internal regions were determined. Two peptide sequences of 25 and 12 residues were used to construct degenerate oligonucleotides for polymerase chain reaction (PCR) amplification of a 450-nucleotide fragment of the BAMT coding region (see protocol above). The amplified fragment was in turn used to isolate cDNAs from a petal-specific Anthirrinum cDNA library. Several cDNA clones, all containing the same open reading frame of 364 codons (starting with a methionine codon) were isolated and sequenced. The protein encoded by these cDNAs contains all six peptide sequences determined experimentally.

The sequence of the BAMT protein does not contain the consensus motifs found in many plant SAM-dependent O-methyl transferases (Ibrahim, 1997; Ibrahim et al., 1998; Joshi and Chiang, 1998). However, the predicted amino acid sequence of the BAMT protein is approximately 40% identical to salicylic acid carboxyl methyl transferase recently isolated from C. breweri (Ross et al., 1999) (FIG. 4). These enzymes thus define a new class of plant carboxyl methyl transferases. They share the ability to transfer the methyl group of SAM to a free carboxyl group.

Database searches revealed sequences for eight unidentified proteins with 20 to 40% identity to BAMT. All of these sequences are encoded by Arabidopsis genes and predict to contain of 360–370 amino acid residues. These proteins might all belong to a class of carboxyl methyl transferases with different substrate specificity. The sequences of two hypothetical proteins with the highest identity to BAMT are also shown in FIG. 4. In addition, there are a number of expressed sequence tags in the databases with similarity to BAMT.

EXAMPLE 4

Functional Expression of BAMT cDNA in Escherichia coli

Expression of BAMT in Escherichia coli

The coding region of benzoic acid carboxyl methyl transferase (BAMT) was amplified with the sense 29-mer oligonucleotide 5'-GTCTAGACATATGAAAGTGATGAAGAAAC-3', shown in SEQ ID NO:5 (the first nucleotide is used to increase the melting temperature of the oligonucleotide, the next 6 nucleotides represent the XbaI recognition sequence, the following 3 nucleotides represent the first 3 nucleotides of the NdeI recognition sequence and the last 19 nucleotides represent nucleotides 19–37 of SEQ ID NO:1), that introduced an NdeI site at the initiating ATG codon and the antisense 29-mer oligonucleotide 5'-TGGATCCTTCATCTCCTACTTAGAGAAAC-3', shown in SEQ ID NO:6 (the first nucleotide is used to increase the melting temperature of the oligonucleotide, the next 6 nucleotides represent the BamH1 recognition sequence and the last 22 nucleotides represent a sequence complementary to nucleotides 1093–1114 of SEQ ID NO:1), that introduced a BamHI site downstream of the stop codon. The PCR-amplified 1.1-kb fragment was cloned into the NdeI-BamHI site of the expression vector the pET-T7 (11a) (Novagen, Carlsbad, Calif.), Escherichia coli BL21 (DE3) cells were transformed with recombinant plasmid, and the expression of BAMT cDNA was induced by the addition of 0.4 mM isopropyl β-D-thiogalactopyranoside at $A_{600}$ of 0.5 with a 20-h incubation at 20° C.. (Yamaguchi et al., 1996). E. coli cells were harvested by centrifugation and sonicated, and BAMT activity was measured in soluble and insoluble fractions.

Extraction of Methyl Benzoate from the Medium of E. coli cells and Gas Chromatography—Mass Spectrometry Analysis BL21 (DE3) cells expressing BAMT and those containing pET-T7 (11a) vector (controls) were grown in the presence (5 μg/mL) and absence of benzoic acid under the conditions described above. After harvesting the cells by centrifugation, the cultured medium (25 mL) was extracted with 5 mL of hexane, and the hexane phase was concentrated to 200 μL and analyzed by gas chromatography—mass spectrometry (Dudareva et al., 1998a).

Results

Figure 5:
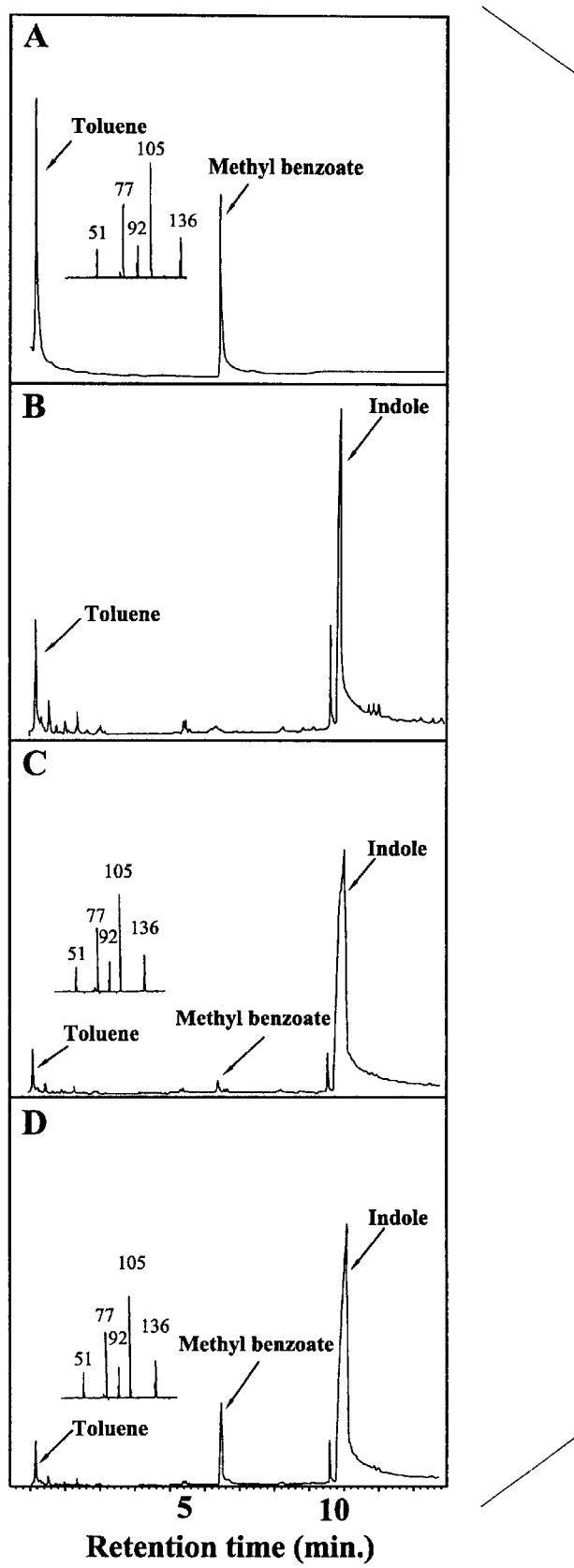
FIGS. 5A–5D depict GC-MS analyses, obtained as described in Example 4, showing detection of methyl benzoate in the medium of *E. coli* cells expressing Snapdragon BAMT.

To verify that the isolated cDNA clone encodes BAMT, we expressed the protein in Escherichia coli. When cell lysates were tested with benzoic acid, salicylic acid, cinnamic acid and their derivatives, high activity (7.53 pkat/mg protein) was detected with benzoic acid, and no activity with any of the other substrates. Moreover, the cultured medium of the E. coli cells expressing BAMT contained a small amount of methyl benzoate (0.1 μg/mL) (FIGS. 5A and 5C). The amount of methyl benzoate in the medium increased to 0.66 μg/mL when the growing medium was supplemented with 5 μg/mL benzoic acid (FIGS. 5A and 5D). E. coli cells that contained a pET-T7 (11a) plasmid without the BAMT coding region did not have any detectable BAMT activity and did not produce methyl benzoate (FIG. 5B). For FIG. 5C, the growing medium was not supplemented with benzoic acid whereas for FIG. 5D, the growing medium was supplemented with 5 ug/ml benzoic acid. In FIGS. 5C and 5D, the mass spectrum is that of the peak eluted at the same retention time as the authentic methyl benzoate standard in FIG. 5A.

EXAMPLE 5

Tissue- and Developmental Stage-specific BAMT Expression

RNA Isolation and RNA Gel Blot Analysis

Total RNA from floral tissues and petals at different stages of flower development was isolated and analyzed as previously described (Dudareva et al., 1996; 1998a; Wang et al., 1997). The yield of total RNA from upper and lower petal lobes per gram fresh weight of tissue at different stages of development was very similar varying from 120 to 190 μg. A 1.3-kb EcoRI fragment containing the coding region of the BAMT gene was used as a probe for RNA gel blot analysis. For determination of tissue-specific expression, 7 μg of total RNA was loaded in each lane; to determine variations in expression over the life span of the flower, 3 μg of total RNA was loaded. Hybridization signals were quantified using Storm 860 Phosphor Imager (Molecular Dynamics, Sunnyvale, Calif.), and BAMT mRNA transcript levels were normalized to rRNA levels to overcome error in RNA quantitation by spectrophotometry. Autoradiography was performed for 24 hours.

Immunoblots

Crude extracts were prepared from upper and lower petal lobes of snapdragon flowers at different stages of flower development (mature buds one day before opening to day 12 after anthesis), as described previously (Dudareva et al., 1996). Immunodetection was performed using rabbit anti-BAMT purified polyclonal antibodies (1:2500 dilution) with goat anti-rabbit IgG horseradish peroxidase conjugate (1:30 000 dilution) as secondary antibody. Antigen bands were visualized using Western Blot Chemiluminescence reagent (New England Nuclear Life Science Products, Boston, Mass.), according to the manufacturer's protocols, exposed on Kodak X-OMAT AR film (Eastman Kodak Company, Rochester, N.Y.), and quantified by densitometry. Preimmune serum was used as a control. Quantitation of immunoblots was conducted using the Scion Image 1.62c Software package (Scion Corporation, Frederick, Md.).

Results

Figure 6A:
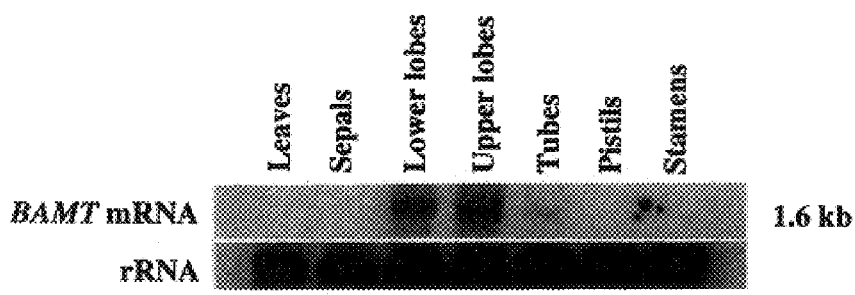
FIGS. 6A–6B depict RNA gel blot analysis of BAMT mRNA.
Figure 6B:
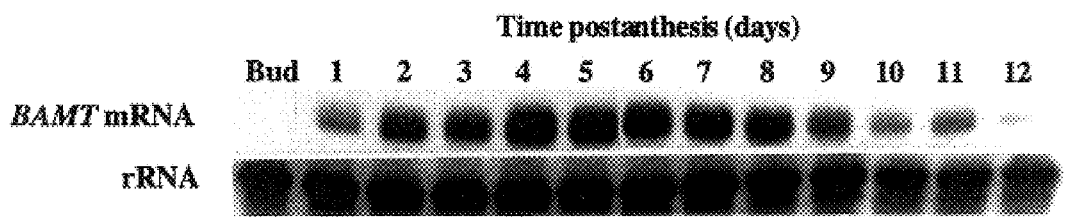

RNA gel blot analysis was used to determine the tissue specificity of BAMT gene expression. The highest levels of BAMT mRNA were observed in the upper and lower lobes of petals (FIG. 6A). A low level of BAMT transcripts was also detected in the tube. No detectable signals were found in pistils, stamens, sepals and leaf tissue. Because BAMT activity and BAMT mRNA were found mostly in upper and lower lobes of petals, we examined the steady state levels of BAMT mRNA in Maryland True Pink petals during flower development. BAMT mRNA was first detected in 1-day-old flowers, and its level increased until it peaked on day 4 after anthesis (FIG. 6B and C). Day 6 after anthesis, mRNA levels declined 30% from the peak level, remained relatively stable until day 9, and decreased thereafter.

Figure 7A:
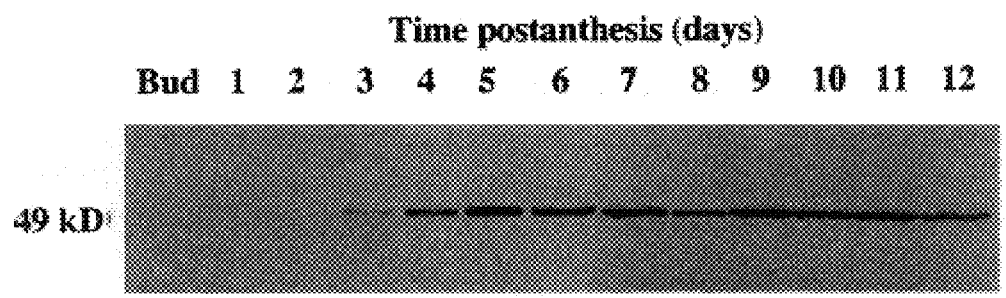
FIGS. 7A depicts a protein gel blot analysis of BAMT protein levels in upper and lower lobes of snapdragon petals at different stages of development as described in Example 5. Representative protein gel blots show the 49-kD protein recognized by anti-BAMT antibodies. Proteins were extracted from upper and lower petal lobes at different stages of development, and 20 μg of protein was loaded in each lane.
Figure 7B:
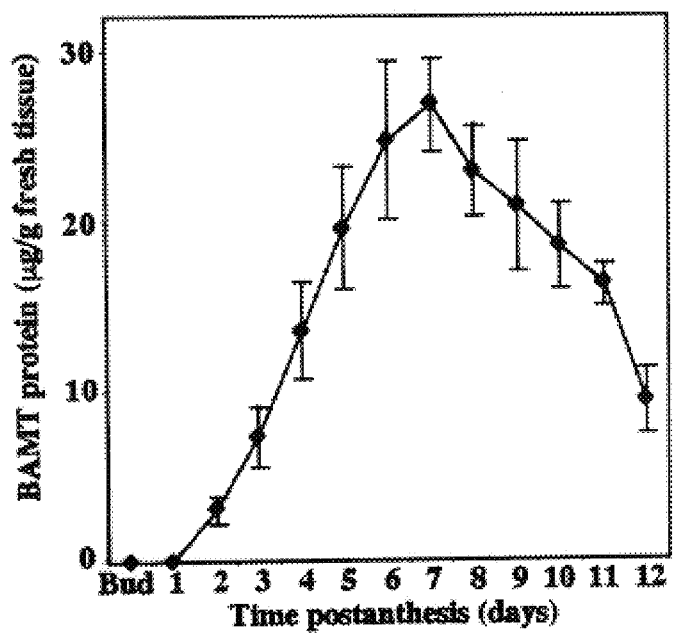
FIG. 7B is a graphical plot of the variations in levels of the BAMT protein in upper and lower petal lobes throughout the life span of the flower as described in Example 5. Values were obtained by scanning the protein gel blots. Each point is the average of seven different experiments (including the one shown in FIG. 7A). Standard error values are indicated as vertical bars.

The levels of BAMT protein in upper and lower petal lobes of snapdragon flowers over the developmental period from mature buds to day 12 after anthesis were quantitatively determined by using the chemiluminescence protein gel blotting technique. The polyclonal anti-BAMT antibodies, raised against the denatured BAMT protein overexpressed in E. coli, selectively recognized one protein with an apparent molecular mass of 49 kD in crude petal extracts separated by SDS-PAGE. The BAMT protein was first detected in 2-day-old flowers, indicating a very low amount of this protein in younger flowers (FIG. 7A). Compared to the mRNA, the level of BAMT protein was highest on day 7 after anthesis (FIG. 7B).

EXAMPLE 6

Accumulation of Benzoic Acid in Petal Tissues of Snapdragon Flowers

Extraction and Quantification of Endogenous Benzoic Acid

Benzoic acid was extracted using supercritical carbon dioxide extraction at 414 bars and 40° C. using SFX-210 Extractor outfitted with a 2600 pump and a temperature controlled variable restrictor (ISCO Inc., Lincoln, Nebr.) (McHugh and Krukonis, 1994). Four grams of petal tissues (upper and lower lobes) at different stages of flower development were extracted with 440 mL of $CO_2$ at a flow rate of about 7 mL/min. Extracts were collected in a test tube filled with 4 mL of methanol, filtered through 0.2 $\mu$m pore-size nylon filters (Nalgene, Rochester, N.Y.) to eliminate insoluble debris, and concentrated to 150 $\mu$L. The samples (25 $\mu$L) were injected and the compounds were separated on a C18 reverse phase HPLC column (Hibar Ec Cartridge containing Merk Lichrosorb RP-18 10-$\mu$m C18 reverse phase packing; 4.6 mm×25 cm [Alltech Associates, Deerfield, Ill.]) maintained at 20° C. (Graham, 1991). Benzoic acid was separated during a 15-min gradient of methanol (25–70%) and quantified by UV absorption at 210 nm (Varian 9050, variable wavelength UV-VIS detector, Varian Chromatography Systems, Walnut Creek, Calif.). Under these conditions, retention time for benzoic acid was 8.6 min, and the limit of detection was 6 $\mu$g/mL of benzoic acid (0.15 $\mu$g per injection). Standard solutions containing 6 $\mu$g/mL–120 $\mu$g/mL of authentic benzoic acid were used to prepare a standard curve. All data were corrected for benzoic acid recovery, using internally spiked samples.

Benzoic acid in plant extracts was verified by mass spectrometric analysis and also confirmed by its coelution with authentic standard using HPLC. For GC-MS analysis, the benzoic acid peak was collected from the HPLC column and derivatized by adding bis(trimethylsilyl) trifluoroacetamide (Supelco, Bellefonte, Pa.) which makes a trimethylsilyl ester of benzoic acid. The derivatized sample was analyzed by FinniganMAT GCQ mass spectrometer. Obtained gas chromatography—mass spectrometry spectrum was compared with authentic benzoic acid derivatized in the same way.

Results

Figure 8:
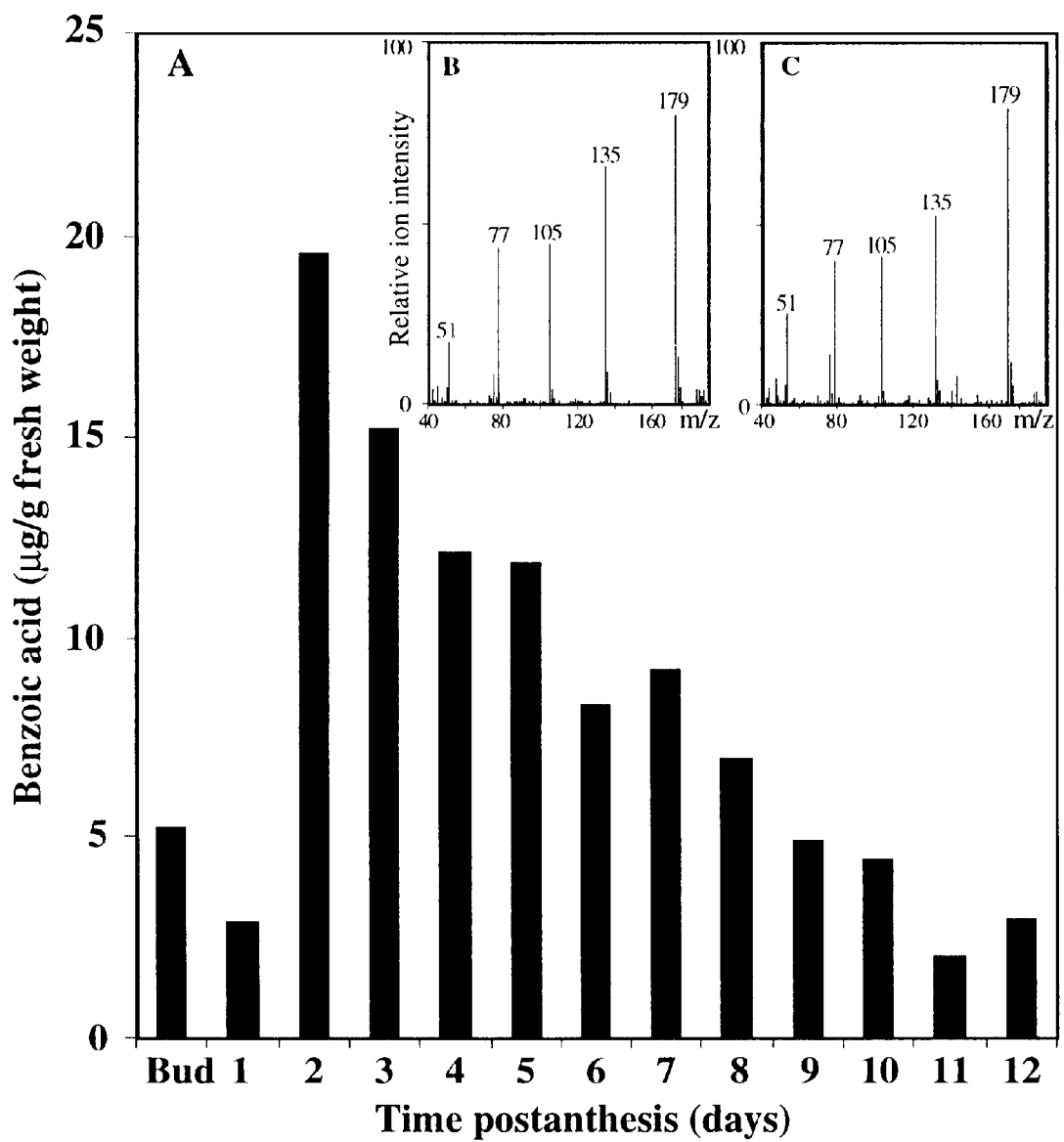
FIG. 8A depicts a graph showing developmental changes in the amount of benzoic acid in upper and lower lobes of snapdragon petals as described in Example 6.
FIGS. 8B–8C depict electron impact mass spectra (EIMS) as described in Example 6.

Because BAMT catalyzes the final step in the biosynthesis of methyl benzoate, regulation of the production of methyl benzoate could also occur at earlier biochemical steps in the pathway. To test this hypothesis, the endogenous pools of benzoic acid were measured in petal tissue during flower development. A substantial endogenous pool of benzoic acid was found in petal tissue (upper and lower lobes), and the size of this pool changed during development (FIG. 8). The highest content of benzoic acid was found on the second day after anthesis (19.6 $\mu$g/g fresh weight) (FIG. 8A), when the emission of methyl benzoate and the activity of BAMT are relatively low (about 30% of the maximum level) (FIGS. 1A and 3D). The petal concentration of benzoic acid declined coincident with the increasing levels of BAMT activity and emission of methyl benzoate up to the eighth day after anthesis. After that time, the amount of benzoic acid continued to decrease, whereas the level of BAMT activity remains relatively high (FIGS. 8A and 3D). Thus, the low emission of methyl benzoate in older flowers (FIG. 1A) could be due to the limited amount of benzoic acid.

Analysis

Temporal and Rhythmic Variations in Methyl Benzoate Emission

Flowers of many plant species attract pollinators by producing different complex mixtures of volatile compounds that give each species unique, characteristic fragrances. Volatile compounds emitted from flowers play a prominent role in the localization and selection of flowers by insects (Dobson, 1994). Although to date very little is known about the effect of individual scent volatiles on insect-flower interactions, it has been shown, by measuring the electroantennogram responses of insects, that aromatic esters are important floral attractants (Henning and Teuber, 1992; Raguso et al., 1996; Raguso and Light, 1998).

The results described herein show that newly opened young flowers, which are not ready to function as pollen donors because their anthers have not yet dehisced, produce fewer odors, and are less attractive to pollinators than are older flowers (FIG. 1A). A recent investigation of the frequency and duration of bumblebee visits to snapdragon flowers revealed that 1- and 2-day-old flowers received fewer and shorter visits than 4-day-old and older flowers (Jones et al. 1998).

Whereas many plants continuously emit volatile compounds at a constant level during flowering, other flowering plants emit scent in a rhythmic manner with a diurnal or nocturnal maximum (Matile and Altenburger, 1988; Loughrin et al., 1990; Nielsen et al., 1995; Helsper et al., 1998). The rhythmic release of volatiles from some flowers is often correlated with the corresponding temporal activity of their known pollinators (Loughrin et al., 1990, Schiestl et al., 1997). Because snapdragon flowers are pollinated by bumblebees during the daytime, it was expected that flowers would emit lower amounts of volatiles during night versus day. In fact, the amount of methyl benzoate released per hour by a single snapdragon flower was four times higher during the daytime than at the night (FIG. 1B). Emission of methyl benzoate follows diurnal cycles, with the highest emission rate between 9 a.m. and 4 p.m. (FIG. 1B) and coincides with peak foraging activity of bumblebees (Heinrich, 1979).

Biosynthesis of Methyl Benzoate in Floral Tissues and at Different Stages of Flower Development The total activity of BAMT, which is the final enzyme in the biosynthesis of the volatile ester methyl benzoate, was highest in upper and lower lobes of petals, suggesting that these parts of the petals are primarily responsible for the production and emission of methyl benzoate (FIG. 3C). In flowers of many plant species, it has been found that petals are the principal emitters of volatiles (Dobson, 1994; Dudareva et al., 1999). By dissecting snapdragon petals further, it has been shown in the present study that production of floral volatiles in snapdragon flower is even more restricted, being limited mostly to the upper and lower lobes of the petals. In flowers like snapdragon, pollinators must open the petals after landing to gain access to the nectar.

Upper and lower lobes of the petals are the ones that come into contact with the bee's body during landing (FIG. 3A and B). In this way, the bees can accumulate floral scent molecules on their body surface and carry them to the nest, and this floral scent, in turn, can help the bee to recruit new foragers to locate the flowers. It has been shown that the recruitment rate can be increased by intensifying the odor at a food source (Von Frisch, 1971).

In the present study, it has also been found that the level of BAMT activity in upper and lower petal lobes is developmentally regulated. Total BAMT activity gradually increased during the first 5 days after anthesis, as did the emission of methyl benzoate (FIGS. 3D and 1A), remained relatively stable during the next 5 days, although the emission of methyl benzoate declined, and decreased afterward. In *C. breweri* flowers, it has been found that the activities of four enzymes involved in floral scent production follow two different developmental patterns. The activities of two enzymes, S-linalool synthase and S-adenosyl-L-methionine:salicylic acid carboxyl methyl transferase, increased in young flowers and declined in old (5-day-old) flowers, but remained relatively high (40 to 50% from the maximum level) even though emission of linalool and methyl salicylate had practically ceased. The activities of two other enzymes, SAM:(iso)eugenol O-methyl transferase and acetyl-coenzyme A:benzyl alcohol acetyltransferase, showed 10% or less decline at the end of the life span of the flower, although emissions of corresponding volatile compounds did decline substantially (Dudareva and Pichersky, 2000). The BAMT enzyme from snapdragon flowers appears to belong to the first group, because its activity declined at the end of the life span of the flower (9 to 12 days after anthesis), being 46% of the maximum level, without the concomitant emission of methyl benzoate (FIGS. 3D and 1A).

Regulation of Methyl Benzoate Emission in Snapdragon Flowers

Figure 6C:
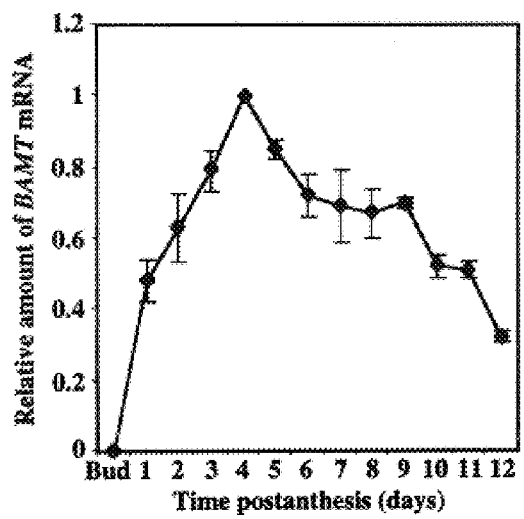
FIG. 6C is a graph of the variations in levels of BAMT mRNA in upper and lower petal lobes throughout the life span of the flower. Values were obtained by scanning RNA blots by using a Phosphor Imager as described in Example 5. Each point is the average of five different experiments (including the one shown in FIG. 6A), and values were corrected by standardizing for 18S rRNA levels.
Figure 9A:
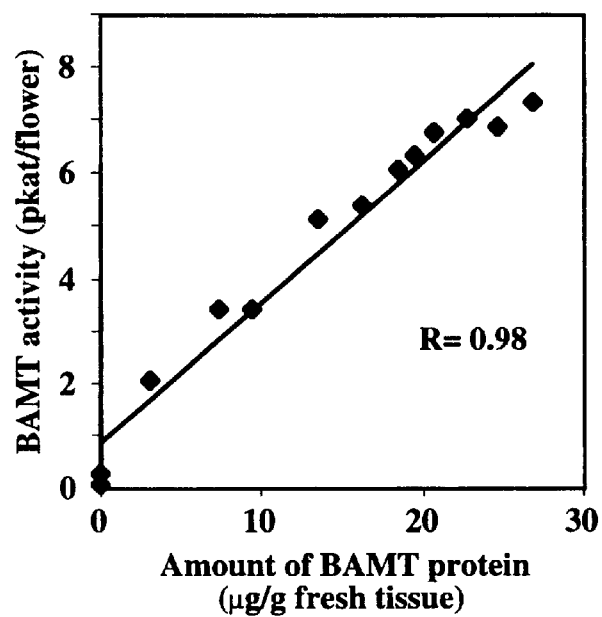
FIGS. 9A and 9B depict graphical representations of BAMT activity versus amount of BAMT protein, and methyl benzoate emission versus predicted methyl benzoate production, respectively, during the lifespan of the snapdragon flower as described in Example 6.

Recent progress in understanding of floral scent production in plants, based so far only on *C. breweri* as the model system, has indicated that scent compounds are synthesized de novo in the epidermal cells of floral organs from which they are emitted (primarily the petals). The activity levels of enzymes involved in scent production and, indirectly, scent emission, are regulated mainly at the transcriptional levels at the site of emission (Dudareva et al., 1996, 1998a; Wang et al., 1997). The results described herein demonstrate that, of the different parts of snapdragon flower, the upper and lower lobes of petals contain the majority of BAMT transcripts (FIG. 6A). These mRNA levels strongly correlate with the BAMT activity profile (FIG. 3C), where high enzyme activity was found only in petals, and very low or no activity was detected in other floral organs and leaves. The steady state levels of BAMT mRNA in petals is developmentally regulated, being highest on day 4 after anthesis (FIGS. 6B and 6C). The levels of methyl benzoate emission, and BAMT activity and mRNA in petals all rise and fall in simultaneously until the end of the life span of the flower, with mRNA levels peaking one day ahead of enzyme activity and emission (FIGS. 1A, 3D, and 6C). A positive correlation between levels of emission, enzyme activity, and mRNA indicates that similar to *C. breweri* BAMT enzyme activity is regulated primarily at a pretranslational level. When BAMT activity at different stages of flower development was plotted against the amount of protein, linear regression analysis revealed a correlation coefficient of 0.98 (FIG. 9A). Such a strong correlation between enzyme activity and protein provides compelling evidence that differences in BAMT activity at different stages of development are due to changes in the abundance of BAMT protein rather than post-translational modification. These results suggest that similar to *C. breweri*, the levels of activity of scent biosynthetic enzymes in snapdragon are regulated by transcription of the corresponding genes in the flower.

Figure 9B:
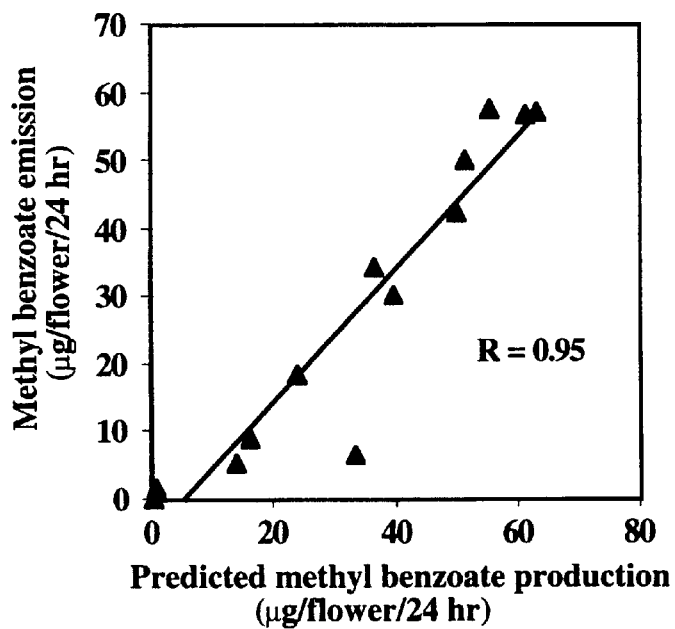

Because BAMT is the final enzyme in the biosynthesis of methyl benzoate (FIG. 2), the regulation of methyl benzoate production could also occur at earlier biochemical steps in the pathway by controlling the supply of the substrate, benzoic acid. Data presented in this study show that the levels of the benzoic acid pools in upper and lower petal lobes are indeed developmentally regulated (FIG. 8A). The low level of benzoic acid in old flower petals (9–12 days after anthesis) may indicate that the earlier biochemical steps in the pathway are blocked as the flower ages or that synthesized benzoic acid is required for some other processes in the cells. When the emission of methyl benzoate from snapdragon flowers was plotted against predicted production of methyl benzoate (FIG. 9B; see the protocol above for details), linear regression analysis revealed a correlation coefficient of 0.95, indicating that production of methyl benzoate is regulated by the amount of benzoic acid and by the amount of BAMT protein, which in turn is regulated at the transcriptional level.

We found that emission of methyl benzoate declines toward the end of the life span of the flower (9 to 12 days after anthesis) (FIG. 1A), whereas BAMT activity remains relatively high (46% from the maximum level) (FIG. 3D). Interestingly, BAMT activity in 3- and 12-day-old flowers are similar (3.4 pkat per flower) (FIG. 3D), indicating that the protein in old flowers is capable of producing the same amount of methyl benzoate as 3-day-old flowers. However the level of emission is almost seven times higher in young flowers than in old ones (FIG. 1A). The amount of benzoic acid in petal tissue of 12-day-old flowers is five times lower than in 3-day-old flowers (FIG. 8A), indicating that the level of substrate is a limiting factor.

The high levels of activity of biosynthetic enzymes in old flowers without concomitant emission of volatile products were also found in *C. breweri* (Pichersky et al., 1994; Dudareva et al., 1998b, Wang et al., 1997), but in those cases, the pools of the substrates were not determined. The current data herein shows that the total amount of substrate in the cell is involved in regulation of biosynthesis and emission of flower volatiles, and that the low emission of methyl benzoate in old flowers is due to low levels of benzoic acid in petal tissue (FIGS. 8A and 9B) (it is of course possible that the amount of SAM is also low at the end of the flower's life).

Overall, the results described herein with snapdragon flowers, together with the data obtained in *C. breweri* suggest that common regulatory mechanisms are involved in floral scent production in different plant species. This study contributes additional evidence that in both *C. breweri* flowers and snapdragon, scent compounds are produced de novo in the tissues from which they are emitted.

EXAMPLE 7

Purification and Characterization of BAMT

Plant Material

Maryland True Pink snapdragon cultivar (*Antirrhinum majus*) (Ball Seed Co., IL, USA) was grown under standard greenhouse conditions, as described above in reference to Example 1. Upper and lower petal lobes of 5 to 10 day-old flowers were used for enzyme isolation as a floral tissue with the highest BAMT specific activity.

Enzyme Extraction

All extraction and purification procedures were carried out at 4° C. except as noted. Freshly excised upper and lower petal lobes of snapdragon flowers were frozen in liquid $N_2$ and ground to a fine powder using a mortar and pestle. The frozen powder was immediately slurried with extraction buffer (5:1 (v/w) buffer: tissue) containing 50 mM Bis-Tris-HCl, pH 6.9, 10 mM β-mercaptoethanol, 5 mM $Na_2S_2O_5$, 1% (w/V) polyvinylpyrrolidone (PVP-40), 1 mM phenyl-methanesulfonyl fluoride, and 10% (v/v) glycerol. The slurry was additionally homogenized in a chilled glass homogenizer (Wheaton, VWR Scientific Products), passed through two layers of Miracloth (Calbiochem, CA) and centrifuged for 10 min at 12000 g. The pellet was discarded and the supernatant that contained the BAMT activity was used as the enzyme source.

BAMT Enzyme Activity

To monitor the BAMT elution profile during purification, enzyme assays were performed as described in Example 2. Enzyme activity was determined by measuring transfer of the $^{14}C$-labeled methyl group of SAM to the carboxyl group of benzoic acid. The standard reaction mixture (100 μL) consisted of 20 μL of crude extract (25–40 μg of protein), 100 μM of S-adenosyl-L-methionine (SAM; containing 0.1 μCi of S-[methyl-$^{14}C$] adenosyl-L-Met (NEN Life Science Products, Boston, Mass.) in assay buffer (50 mM Tris-HCl pH 7.5, and 3 mM 2-mercaptoethanol), containing 2 mM benzoic acid and 0.5 mM EDTA. After incubation for 30 min at 20° C., the radioactively labeled methylated product was extracted by the addition of 100 μL hexane, and 50 μL of the organic phase was counted in a liquid scintillation counter (model LS 6800, Beckman, Fullerton, Calif.). In assays for pH optimum, cofactor requirements, and $K_m$ measurements, proper concentrations of purified BAMT were chosen so that the reaction velocity was proportional to enzyme concentration and was linear with respect to time for at least 30 min. Protein concentration was determined by the Bradford method (1976) using the Bio-Rad protein reagent and bovine serum albumin as a standard.

Protein Purification

In a typical purification procedure, 125 mL of crude extract (representing 25 g fresh weight of petal tissue) were loaded onto a DEAE-cellulose column (10 mL of DE53, Whatman, N.J.) preequilibrated with a solution containing 50 mM Bis-Tris-HCl, pH 6.9, 10% glycerol and 10 mM β-mercaptoethanol (buffer A) at a flow rate of about 1 mL/min. After washing off unabsorbed material from the column with 30 mL of buffer A, BAMT was eluted with a linear gradient (60 mL) from 0 to 400 mM KCl in buffer A. Fractions (2 mL) were collected and assayed for BAMT activity. Fractions with the highest BAMT activity in the 180–280 mM KCl range were pooled (total of 26 mL) and loaded on a Phenyl Sepharose 6 Fast Flow (low sub, level of phenyl substitution 20 μmole per ml gel) column (0.7×2.5 cm, Pharmacia Biotech Inc., N.J.) attached to a Pharmacia FPLC apparatus and preequilibrated with 300 mM KCl in buffer A at a flow rate of 0.2 mL/min. After the enzyme was loaded, the column was washed with 3 mL 300 mM KCl in buffer A and eluted with a linear reverse gradient (4 mL) from 300 mM KCl in buffer A to water followed by an additional 11 mL of water. Fractions of 0.7 ml were collected into tubes containing 100 μL 1 M KCl, 100 μL glycerol, 100 μL of 0.5 M Bis-Tris-HCl, pH 6.9 and 1 μL of 14 M β-mercaptoethanol. The fractions containing BAMT activity, eluted with water, were pooled (7 mL) and subjected to ion-exchange chromatography on a Mono-Q column using the FPLC system. The column was previously equilibrate with 100 mM KCl in buffer A. After loading the protein onto the column, the column was washed with 100 mM KCl in buffer A and the bound protein was eluted using a 10 mL linear (100–400 mM) gradient of KCl in buffer A followed by an additional 5 mL of buffer A containing 400 mM KCl, at flow rate of 0.25 mL/min. The enzyme consistently eluted at about 360 mM KCl. Fractions (0.5 mL each) were collected and protein content and purity were examined by SDS-PAGE gel electrophoresis followed by staining of the gel with Coomassie Brilliant Blue. Fractions which had the largest amount of pure protein were used for N-terminal sequencing, internal peptide sequencing, and initial enzyme characterization.

Expression of BAMT in *E. coli* and Protein Purification

The coding region of BAMT was amplified with sense 29-mer oligonucleotide 5'-GTCTAGACATATGAAAGTGATGAAGAAAC-3' (for the first methionine codon), shown in SEQ ID NO:5 (as described in Example 4), or 27-mer oligonucleotide 5'-CTCTAGACATATGAAGAAACTTTTGTG-3' (for the second methionine codon), shown in SEQ ID NO:7 (the first nucleotide is used to increase the melting temperature of the oligonucleotide, the next 6 nucleotides represent the XbaI recognition sequence, the following 3 nucleotides represent the first 3 nucleotides of the NdeI recognition sequence and the last 17 nucleotides represent nucleotides 28–44 of SEQ ID NO:1), that introduced an NdeI site at the initiating ATG codon, and the antisense 29-mer oligonucleotide 5'-TGGATCCTTCATCTCCTACTTAGAGAAAC-3', shown in SEQ ID NO:6 (as described in Example 4), that introduced a BamHI site downstream of the stop codon. The PCR-amplified 1.1kb fragment was cloned into the NdeI-BamHI site of the expression vector pET-28a which contains an N-terminal polyhistidine (6×His) tag (Novagen, Inc.). *E. coli* BL21 (DE3) cells were transformed with recombinant plasmid and were grown in LB medium with 50 μg/mL kanamycin at 37° C. When the culture density reached $OD_{600}$ of 0.5, the expression of BAMT cDNA was induced by addition of IPTG to final concentration of 0.4 mM. After 20-h incubation with shaking (200 rpm) at 20° C., *E. coli* cells were harvested by centrifugation and sonicated in lysis buffer, containing 10 mM NaCl, 50 mM Tris-HCl pH 8.0, 1 mM EDTA, 10% glycerol, and 10 mM β-mercaptoethanol. BAMT activity was measured in soluble and insoluble fractions.

The *E. coli*-expressed BAMT protein was purified by nickel-based affinity chromatography (2.5 ml bed volume) according to the manufacturer's protocol (Novagen, Inc). Protein was eluted with 10 ml of stripping buffer (0.5 M NaCl, 20 mM Tris-HCl pH 7.9 and 100 mM EDTA), the fractions containing BAMT activity were pooled and dialyzed against 2 L of buffer A overnight at 4° C.

Molecular Weight Determination

Molecular weight of the native plant BAMT protein was determined by gel filtration on a Superdex 200-HR (Pharmacia Biotech. N.J.) column (1×30 cm) calibrated with the following markers: cytochrome C (12.4 kDa), carbonic anhydrase (29 kDa), ovalbumin (43 kDa), aldehyde dehydrogenase 3 (100 kDa), alcohol dehydrogenase (150 kDa), and β-amylase (200 kDa). Buffer, containing 100 mM Na phosphate pH 7.4, 100 mM NaCl and 0.025% β-mercaptoethanol, was used for column equilibration and elution. Fractions of 0.2 mL were collected at a flow rate of 0.5 mL/min and analyzed for BAMT activity. Denaturing SDS-PAGE was performed on 10% gels to determine the subunit molecular weight. The gels were calibrated with molecular weight standards in the range of 7.4–208 kDa (Bio-Rad, CA).

Temperature Effect on BAMT Stability

Purified BAMT proteins were incubated at temperatures ranging from 4 to 65° C. for 30 min and then chilled on ice. Samples incubated at each temperature were then used for enzyme assays. At least three independent assays were performed for each point and then an average was taken.

pH Optimum of BAMT Activity

The optimum pH for BAMT activity was determined using two buffer systems. Reactions were carried out in 50 mM Tris-HCl buffer with pH ranging from 6.5 to 9.0 and in 50 mM Tris/Na phosphate/Na citrate buffer with pH ranging from 4.0 to 9.5. Final results are an average of four independent assays.

Effectors

Enzyme assays were performed with one of the following cations present in the assay buffer at the final concentration of 5 mM: $Ca^{2+}$, $CU^{2+}$, $Fe^{2+}$, $K^+$, $Mg^{2+}$, $Mn^{2+}$, $Na^+$, $NH_4^+$, and $Zn^{2+}$. Except for $Cu^{2+}$ and $Fe^{2+}$, which precipitate under reducing conditions, all assay buffers also contained 10 mM β-mercaptoethanol. Final results are an average of three independent assays.

Determination of Kinetic Properties

Alternative substrate competition experiments were performed by varying the concentration of one substrate at each of a series of concentrations of the other. Data were presented as double-reciprocal plots of initial velocity (v) versus varying substrate (S) concentrations. In all experiments, appropriate enzyme concentration was chosen so that the reaction velocity was linear during the incubation time period. Substrate interaction studies were done by fixing the concentration of one substrate while changing that of the other. Linear regressions were fitted to the data in double-reciprocal plots. Replots of the data were used to determine the kinetic parameters.

Results and Analysis

Purification of BAMT from Snapdragon Flowers

We have previously shown that BAMT catalyzes the transfer of the methyl group of S-Adenosyl-L-methionine (SAM) to the carboxyl group of benzoic acid to make the volatile ester, methylbenzoate, one of the most abundant scent compounds of snapdragon, Antirrhinum majus. (Dudareva et al., 2000). We have also isolated a snapdragon cDNA clone encoding BAMT and showed that the BAMT gene is only expressed in upper and lower lobes of petals of snapdragon flowers and the levels of BAMT mRNA are positively correlated with BAMT activity. For isolation of a BAMT cDNA, BAMT protein was first purified from snapdragon flowers and subjected to partial peptide sequencing. However, the purification protocol has-not as yet been reported, nor the enzyme characterization with respect to its kinetic properties and other parameters (Dudareva et al., 2000).

Figure 10:
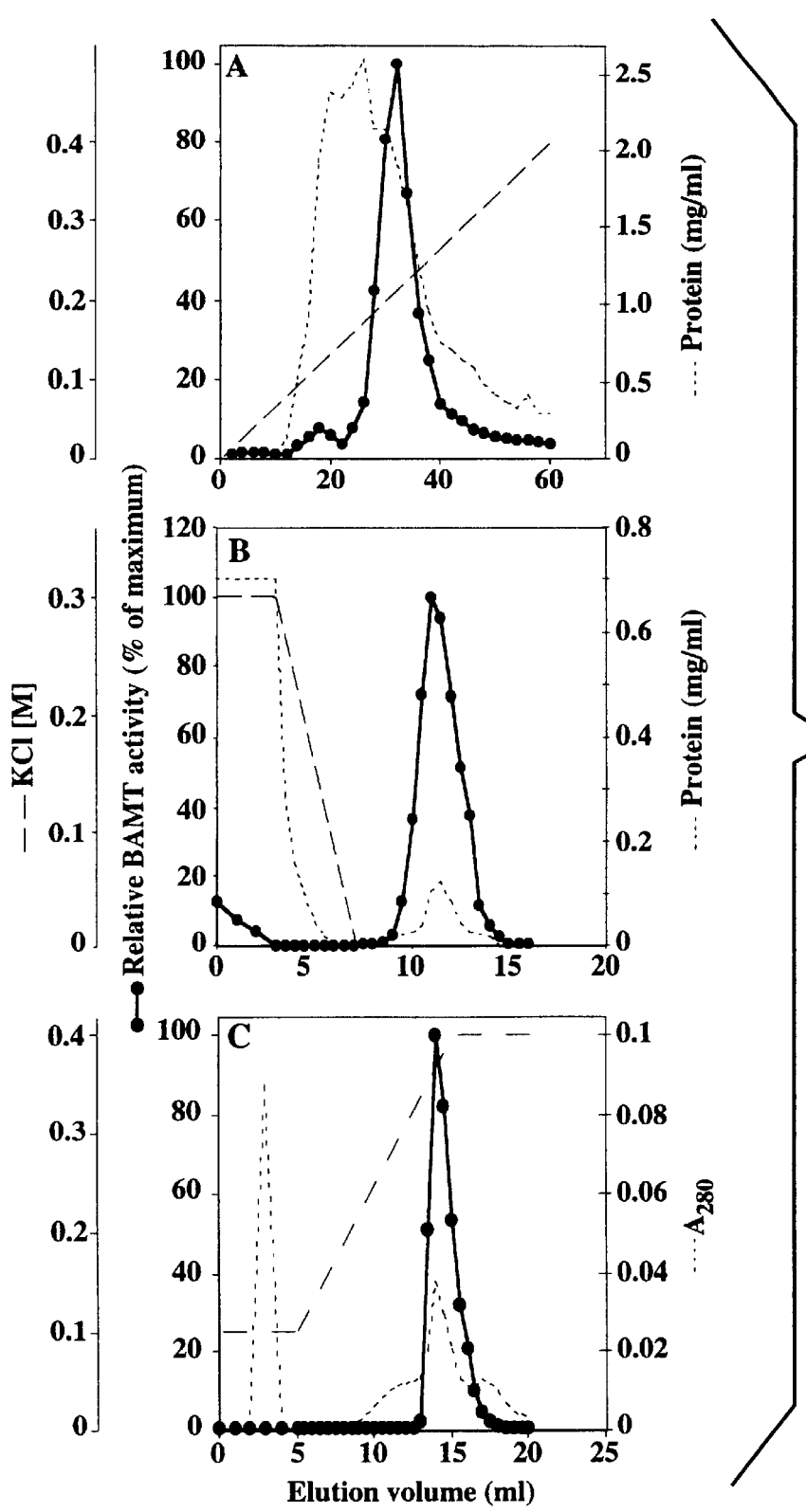
FIGS. 10A–10C depict BAMT activity and the amount of protein from petal tissue of snapdragon flowers as a function of elution volume in various columns as described in Example 7. The purification involved three column chromatographic steps.

In this example, detailed protocols are presented for purification of BAMT protein from crude extract of snapdragon petals and from E. coli cells expressing the Antirrhinum BAMT cDNA and the characterization of the enzyme. Plant BAMT protein was purified from 5- to 1 0-day-old upper and lower petal lobes (floral tissue with the highest BAMT specific activity [Dudareva et al., 2000]) using DE53 anion exchange, Phenyl Sepharose 6FF (low sub) and Mono-Q chromatography (FIG. 10). The key step in the purification procedure was hydrophobic interaction chromatography using Phenyl Sepharose 6FF (low sub) which removed most of the contaminating proteins and yielded a 31-fold purification with recovery of about 8% (Table 2 and FIG. 11).

TABLE 2

BAMT Purification from Antirrhinum majus Petals.

| Purification step | Total protein (mg) | Total activity (pkat) | Specific activity (pkat/mg protein) | Purification (-fold) | Recovery (%) |
|---|---|---|---|---|---|
| Crude extract | 256[a] | 749.6 | 2.9 | 1.0 | 100 |
| DE53 | 40 | 503.5 | 12.6 | 4.3 | 67.2 |
| Phenyl Sepharose | 0.68 | 62.0 | 91.1 | 31 | 8.3 |
| Mono-Q | 0.05 | 16.4 | 327.5 | 112 | 2.2 |

[a]Representing 25 g fresh weight of upper and lower petal lobes of snapdragon flowers.

Figure 11:
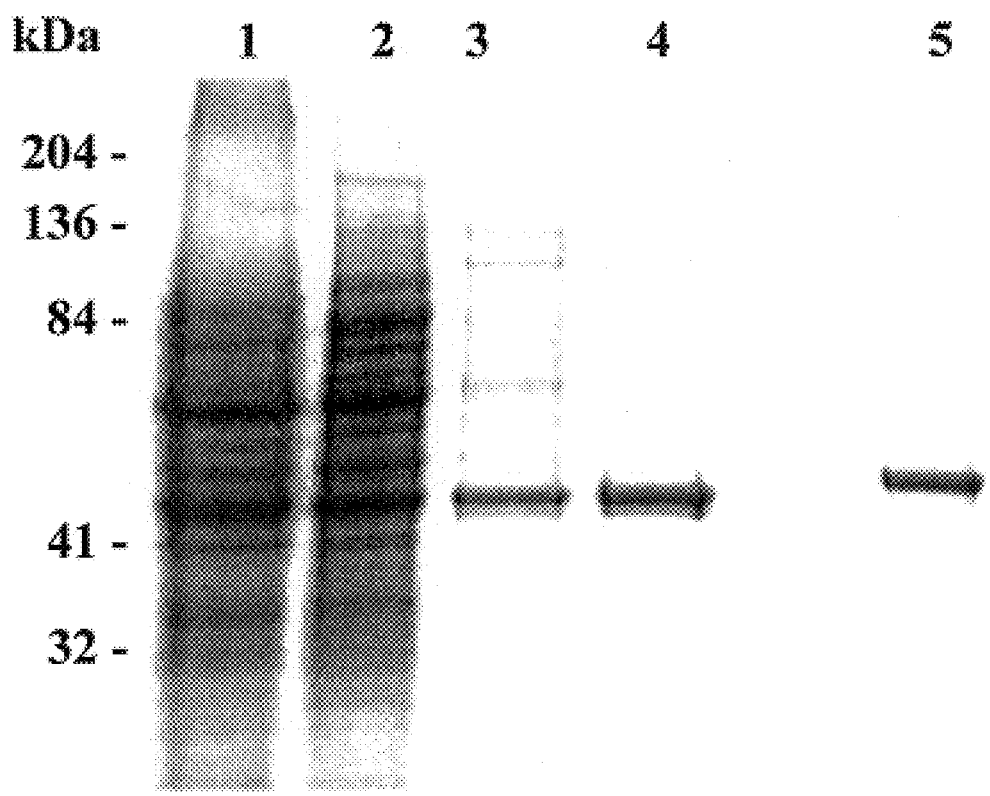
FIG. 11 is a SDS-PAGE analysis of purification stages for BAMT as described in Example 7. Active fractions from each purification step were separated by 13% SDS-PAGE and stained with Coomassie Brilliant Blue. Position of molecular weight markers is indicated on the left. Lane 1, crude extract (about 40 μg); lane 2, DE53 (about 30 μg); lane 3, Phenyl Sepharose (about 5 μg); lane 4, Moho-Q (about 5 μg); lane 5, E. coli expressed BAMT protein (Met$_1$) after purification on nickel column (about 3 μg).

Further purification was achieved by Mono-Q chromatography, which resolved one peak of BAMT activity almost free of contaminants when visualized on SDS-PAGE (FIG. 11). This purification protocol resulted in a 112-fold increase in specific activity over the crude extract with a recovery of 2.2% (Table 2). Starting with 25 g of fresh petal material (256 mg protein), 53 μg of purified BAMT protein was obtained with a specific activity of 327 pkat/mg protein. We have previously shown that this protein has strict substrate specificity for benzoic acid and no activity with several other naturally occurring substrates such as salicylic acid, trans- cinnamic acid and their derivatives (3-hydroxybenzoic acid, 4-hydroxybenzoic acid, 5 benzylalcohol, 2-coumaric, 3-coumaric and 4-coumaric acids) (Dudareva et al., 2000). When purified BAMT protein was subjected to extensive protein sequencing, the amino acid sequences from six internal regions were determined and matched the sequence encoded by a BAMT cDNA (Dudareva et al., 2000). Expression of BAMT cDNA in E. coli also confirmed that the isolated protein is benzoic acid carboxyl methyltransferase, since bacterial cells not only produced enzymatically active protein, but also synthesized a small amount of methylbenzoate and secreted it into the medium (Dudareva et al., 2000).

Figure 12:
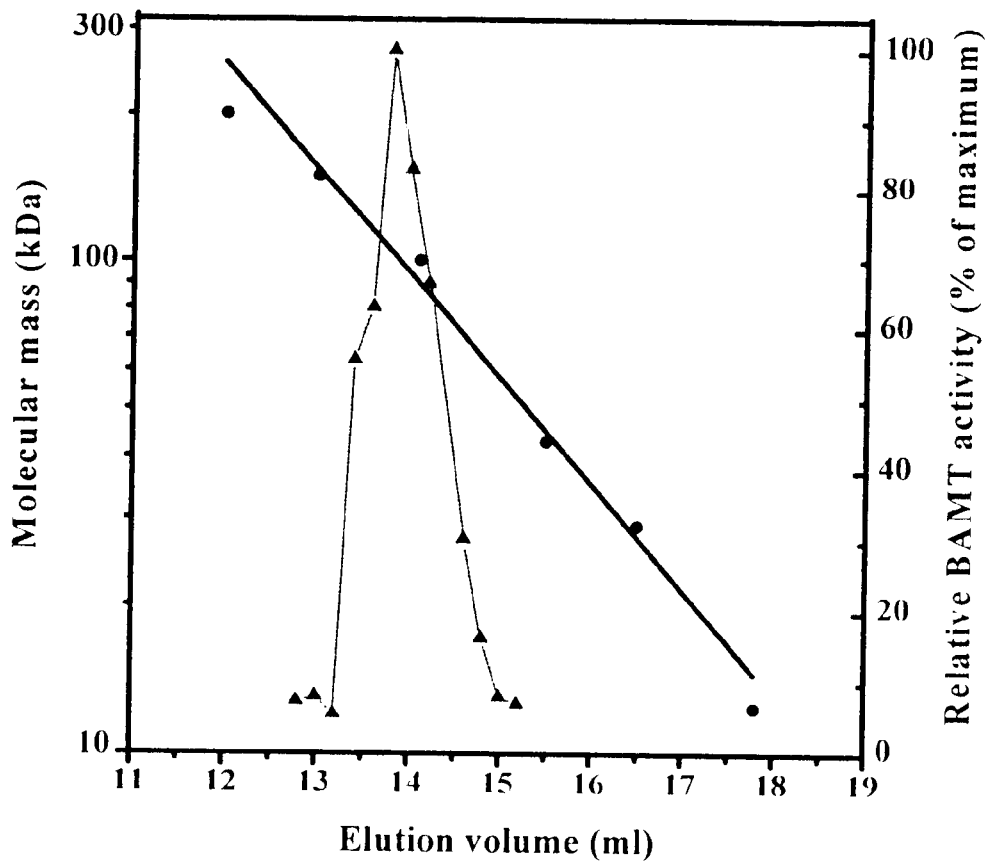
FIG. 12 depicts a graph of molecular mass and BAM activity as a function of elution volume from native gel filtration chromatograph of snapdragon-purified BAMT as described in Example 7.

The molecular mass value of native plant BAMT protein was determined to be 100 kDa from gel filtration chromotography on Superdex 200-HR (FIG. 12), whereas on the SDS-PAGE gels the denatured enzyme exhibited a single band corresponding to a molecular weight of 49 kDa (FIG. 11). These results suggest that the enzymatically active enzyme exists as a homodimer. The calculated molecular mass of the protein encoded by BAMT cDNA is 41 kDa, that is smaller than the apparent molecular mass calculated from its migration in SDS-PAGE gels. Such discrepancies are not uncommon (Oh-oka, et al., 1986; Dudareva et al., 1996; Dudareva et al., 1998a), and in this case may be caused, at least in part, by a relatively high percent (13.9%) of negatively charged residues in the middle part of the protein, and two positively charged clusters at amino and carboxyl ends of the protein.

pH Optimum and Ion Requirements

The pH dependence of BAMT activity was examined in the pH range of 4.0–9.5 using snapdragon BAMT, purified both from snapdragon petal tissue and from E.coli (starting from the first and second methionine codons, see below). The plant-purified BAMT were found to be very similar to the E. coli-expressed snapdragon BAMT. The pH optimum for the BAMT protein was 7.5 with 65% of maximum activity at both pH 6.5 and 8.5. At pH 5.5 and 9.5, the enzyme activity fell to about 50% of the optimal value. The enzyme was active in both Tris- or phosphate-citrate-based buffers. BAMT activity (again, purified both from petals and from *E. coli*) was not affected by the presence of 5 mM $Mg^{2+}$ in the assay reaction. The addition of monovalent cations $K^+$ and $NH_4^+$ stimulated BAMT activity by a factor of 2, whereas the addition of $Fe^{2+}$ and $Cu^{2+}$ has strong inhibitory effect (75–100% inhibition). Other cations such as $Zn^{2+}$, $Na^+$, $Ca^{2+}$, $Mn^{2+}$ affect BAMT activity only slightly (<10%).

Stability of the Enzyme

The purified proteins (both from petal tissue and *E. coli*) were highly stable for several months when stored at −80° C. When stored in buffer A at 4° C., BAMT protein was stable for one week. BAMT was 100% stable for 30 min at 20° C. and 60% stable for 30 min at 30° C. It was 20% stable for 30 min at 42° C. but after 30-min incubation at 65° C. it completely lost activity (not shown).

Kinetic Properties

Kinetic studies were performed using purified plant and *E. coli* expressed BAMT proteins. The BAMT cDNA contains a second methionine codon two codons downstream of the first ATG codon (at position 4 in the protein). Since the N-terminal sequencing of the protein was unsuccessful due to a blocked N terminus, the methionine used as the translational initiation site in planta could not be determined. However, comparisons of the nucleotide sequence around these two ATG codons with the consensus sequences (Lutcke et al., 1987) as well as the fact that in the majority of characterized plant genes the first in-frame methionine codon in the mature mRNA acts as a translational initiation site, suggested that the first ATG in the BAMT cDNA is the initiating codon. The open reading frame was therefore amplified starting with the first methionine codon ($Met_1$) and ligated into the NdeI-BamHI sites of the *E. coli* expression vector pET-28, creating an in-frame fusion with an N-terminal polyhistidine (6×His) tag. To check if BAMT protein retains its enzymatic activity when starting from the second methionine codon and, if so, to characterize its kinetic properties, the BAMT open reading frame was also amplified starting with the second methionine codon ($Met_2$) and ligated into the NdeI-BamHI sites of the pET-28 vector in the same way as described above. All of these constructs (and a pET-28 control plasmid without an insert) were used to transform *E. coli* BL21 (DE3) cells, and expression of foreign gene was induced by IPTG as described above.

Lysates of cells carrying the BAMT constructs ($Met_1$ and $Met_2$) had substantial BAMT activity after IPTG induction as seen in Table 3.

TABLE 3

Plant BAMT Gene Expression in *E. coli* BL21 (DE3) cells[a]

| Construct | Specific activity (pkat/mg protein) | |
|---|---|---|
| | Crude lysates | Purified protein |
| pET-28 | — | — |
| pET-28-BAMT $Met_1$[b] | 9 | 135 |
| pET-28-BAMT $Met_2$[c] | 22 | 140 |

[a]Growing conditions and protein purification are described above. Values are average of four independent experiments.
[b]This construct contains the entire open reading frame of snapdragon BAMT cDNA starting with the first methionine codon. Amount of BAMT protein produced per L of bacterial culture was 1.6 mg.
[c]This construct contains the entire open reading frame of snapdragon BAMT cDNA starting with the second methionine codon, two amino acids downstream of the first one. Amount of BAMT protein produced per L of bacterial culture was 2.7 mg.

Moreover, lysates of cells expressing BAMT $Met_2$ protein had almost 2.4 times higher specific activity than BAMT $Met_1$. This is probably due to either a higher level of protein biosynthesis or stability of $Met_2$ BAMT in *E. coli*. When recombinant enzymes were purified from *E. coli*, specific activities of both enzymes were very similar, being 135 and 140 pcat/mg protein for BAMT protein started from $Met_1$ and $Met_2$, respectively (Table 3).

Figure 13A:
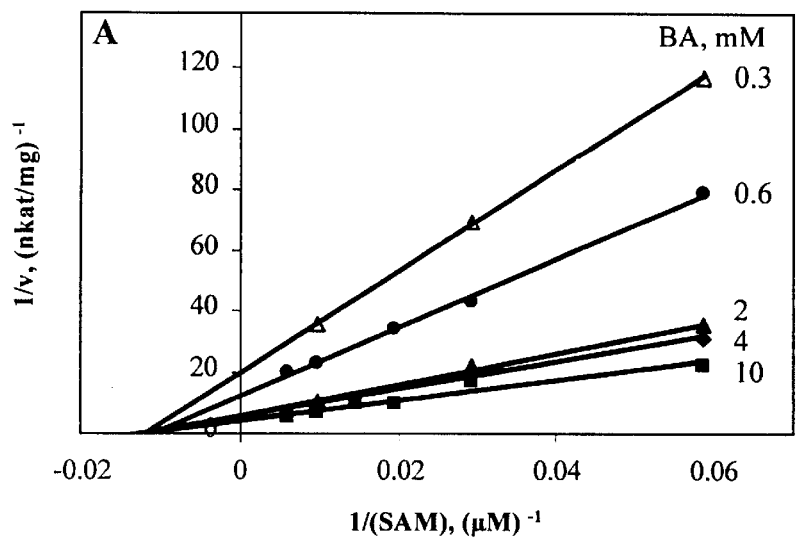
FIGS. 13A–13C depict kinetic analyses of E. coli BAMT protein as described in Example 7.

Substrate interaction kinetics have been performed for purified *E. coli* BAMT ($Met_1$) protein, whereas saturation kinetics were used to measure $K_m$ for plant BAMT and *E. coli* BAMT ($Met_2$). The reaction catalyzed by BAMT exhibited Michaelis-Menten kinetics with respect to its substrate saturation response. The kinetic analysis was consistent with the ordered bi-bi mechanism (FIG. 13A) reported previously for some O-methyltransferases from plants (DeCarolis and Ibrahim, 1989; Maxwell et al., 1992; Attieh et al., 1995). The BAMT ($Met_1$) purified from *E. coli* had apparent $K_m$ values for benzoic acid and SAM of 1.5 mM and 87 μM, respectively. For plant-purified BAMT, the respective $K_m$ values were determined to be 1.1 mM and 28 μM. $K_m$ values for *E. coli* BAMT ($Met_2$) were the same as for *E. coli* BAMT ($Met_1$) protein (Table 4).

TABLE 4

Kinetic parameters of purified plant and *E. coli* expressed BAMT proteins.
Kinetic parameters[a]

| BAMT (origin) | $K_m$BA(mM) | $K_m$SAM(μm) | $V_{max}$ (pkat/mg) | $k_{cat}$ ($sec^{-1}$)[b] |
|---|---|---|---|---|
| Plant | 1.1 | 28 | 220 | 0.02 |
| *E. coli* $Met_1$ | 1.5 | 87 | 300 | 0.03 |
| *E. coli* $Met_2$ | 1.6 | 78 | 300 | 0.03 |

[a]Replots of data from substrate interaction, saturation and product inhibition experiments were used to determine the value of the kinetic parameters.
[b]$k_{cat}$, turnover number of enzyme.

$K_m$ values for benzoic acid were found to be unusually high when compared with $K_m$ values of plant O-methyltransferases for the phenolic substrates, however similar $K_m$ values for substrates have also been found for other plant methyltransferases (Attieh et al., 1995; Sato et al., 1994).

Figure 13B:
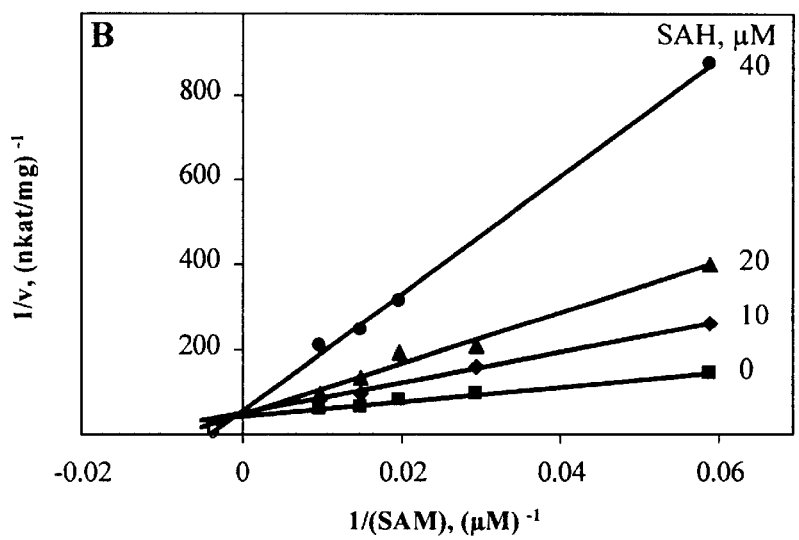
Figure 13C:
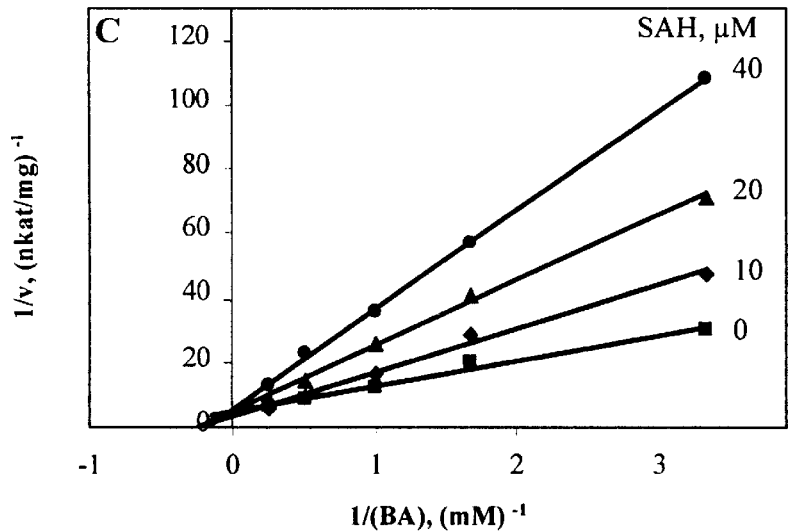

Product inhibition kinetics were used to determine the reaction mechanism of BAMT protein. The last product to be released would act as a competitive inhibitor to the first substrate to bind and as a noncompetitive inhibitor to the second substrate. S-adenosyl-L- homocysteine (SAH) is generally considered to be a potent inhibitor of plant methyltransferases (Poulton, 1981). Product inhibition analysis revealed that inhibition by SAH was competitive with respect to SAM (FIG. 13B) and noncompetitive with respect to BA (FIG. 13C). The $K_i$ value of SAH was determined to be 7 μM for SAM and 14 μM for BA. Since the inhibition by SAH was competitive with respect to SAM and noncompetitive with respect to BA, SAM appears. to be the first substrate to bind to the enzyme. The methylated product, methylbenzoate, would be the first to be released and SAH the last. This pattern was consistent with the ordered bi-bi mechanism whereby the product of the last substrate to bind to the enzyme is the first to be released (Morrison and Ebner, 1971).

Kinetics properties of BAMT suggest the way in which the enzyme may be regulated in plants. Low affinities for BA ($K_m$=1.1 mM) and moderate affinities for SAM ($K_m$=28 μM) with high levels of inhibition by SAH ($K_i$=14 μM) indicate that BAMT activity may be regulated by the intracellular SAM/SAH concentration ratio rather than BA availability. The involvement of SAM/SAH concentration ratios in controlling methyltransferase activities in vivo has been shown in several legumes (Maxwell et al., 1992; Edwards and Dixon, 1991; Fojtova et al., 1998). However, our recent research on floral scent production in Antirrhinum revealed that production of methylbenzoate in petal tissue of snapdragon flowers is regulated by the amount of benzoic acid and by the amount of BAMT protein, which in turn is regulated at the transcriptional level (Dudareva et al., 2000). The concentration of free BA in petal tissue varies from 2 mM on the second day of anthesis to 0.2 mM on the 12 day after anthesis (Dudareva et al., 2000). Since the level of BA in cells is in its $K_m$-value range, BAMT activity in snapdragon flowers during flower development is most likely regulated by availability of BA rather then the SAM/SAH concentration ratios.

BAMT from snapdragon and SAMT from *C. breweri* (Ross et al., 1999) define a new class of carboxyl methyltransferases. These enzymes have in common the ability to transfer the methyl group of SAM to a free carboxyl group of salicylic and benzoic acids with formation of methylsalicylate and methylbenzoate, respectively. SAMT is highly specific for salicylic acid but it does methylate benzoic acid although its $K_m$ value for BA is much higher (Ross et al., 1999). In contrast, BAMT can use only benzoic acid as substrate. Both enzymes are active as dimers with a subunit molecular weight of 40.3 and 41 kDa, respectively. When the properties of BAMT are compared to those of SAMT, it is found that SAMT and BAMT are very similar with respect to their $K_m$ values for SAM (9 $\mu$M and 28 $\mu$M, respectively). However, the $K_m$ value of BAMT for BA (1.1 mM) is much greater than $K_m$ values of SAMT for SA and BA (24 and 190 $\mu$M, respectively) (Ross et al., 1999).

Plant O-methyltransferases known today constitute a distinct superfamily whose members share similarity at common conserved domains that are likely to be involved in SAM and metal binding (Joshi and Chiang, 1998; Ibrahim and Bruneau, et al., 1998). Comparisons of the predicted amino acid sequences of BAMT and SAMT showed that they do not share any significant similarity to previously characterized proteins, including other plant O-methyltransferases (Ross et al., 1999; Dudareva et al., 2000). Isolation and characterization, including structural studies, of other carboxyl methyltransferases with different substrate specificity will provide important information in understanding the function of carboxyl methytransferases.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

REFERENCES

Attieh, J. M., Hanson, A. D., and Saini, H. S. (1995). Purification and characterization of a novel methyltransferase responsible for biosynthesis of halomethanes and methane-thiol in *Brassica oleracea*. *J. Biol. Chem.* 270, 9250–9257.

Bradford, M. M. (1976). A rapid and sensitive method for the quantitation of microgram quantities of protein utilizing the principle of protein-dye binding. *Anal. Biochem.* 72, 248–254.

Coen, E. S., Carpenter, R., and Martin, C. (1986). Transposable elements generate novel spatial patterns of gene expression in *Antirrhinum majus*. *Cell* 47, 285–296.

Coen, E. S., and Meyerowitz, E. M. (1991). The war of the whorls: genetic interactions controlling flower development. *Nature* 353, 31–37.

De Carolis, E., and Ibrahim, R. K. (1989) Purification and kinetics of phenylpropanoid O-methytransferase activites from *Brassica oleracea*. *Biochem. Cell Biol.* 67, 763–769.

Dobson, H. E. M. (1994). Floral volatiles in insect biology. In Insect-Plant Interactions, Vol.V, E. Bernays, ed (CRC Press, Boca Raton, Fla.), pp. 47–81.

Dudareva, N., Cseke, L., Blanc, V. M., and Pichersky, E. (1996). Evolution of floral scent in Clarkia: Novel patterns of S-linalool synthase gene expression in the *C. breweri* flower. *Plant Cell* 8, 1137–1148.

Dudareva, N., D'Auria, J. C., Nam, K. H., Raguso, R. A., and Pichersky, E. (1998a). Acetyl CoA:benzyl alcohol acetyltransferase—an enzyme involved in floral scent production in *Clarkia breweri*. *Plant J.* 14, 297–304.

Dudareva, N., Murfitt, L. M., Mann, C. J., Gorenstein, N., Kolosova, N., Kish, C. M., Bonham, C., and Wood, K. (2000). Developmental regulation of methyl benzoate emission in snapdragon flowers. *Plant Cell* 12, 949–961.

Dudareva, N., Piechulla, B., and Pichersky, E. (1999). Biogenesis of floral scent. *Horticulture Reviews* 24, 31–54.

Dudareva, N., Raguso, R. A., Wang, J., Ross, J. R., and Pichersky, E. (1998b). Floral scent production in *Clarkia breweri*. III. Enzymatic synthesis and emission of benzenoid esters. *Plant Physiol* 116, 599–604.

Dudareva, N., and Pichersky, E. (2000). Biochemical and molecular aspects of floral scents. *Plant Physiol.* 122, 627–634.

Edwards, R., and Dixon, R. A. (1991). Purification and characterization of S-adenosyl-L-methionine:caffeic acid 3-O-methyltransferase from suspension culture of alfalfa (*Medicago sativa* L.) *Phytochemistry* 30, 2597–2606.

Farmer, E. E., and Rayan, C. A. (1990). Interplant communication: airborne methyl jasmonate induces synthesis of proteinase inhibitors in plant lease. *Proc. Natl. Acad. Sci. USA* 87:7713–7716.

Von Frisch, K. (1971). Bees: Their Vision, Chemical Senses, and Language. (Cornell University Press, Ithaca, N.Y.).

Fojtova, M., Kovarik, A., Votruba, I., and Holy, A. (1998). Evaluation of the impact of S-adenosyl-L-homocysteine metabolic pools on cytosine methylation of the tobacco genome. *Eur. J. Biochem.* 252, 347–352.

Gershenzon, J. and Croteau, R. (1991) *Herbivores: their interaction with secondary metabolites*, G. A. Rosenthal, and M. Berenbaum, eds. (Academic Press, New York), pp.165–219.

Graham, T. L. (1991). A rapid, high resolution high performance liquid chromatography profiling procedure for plant and microbial aromatic secondary metabolites. *Plant Physiol* 95, 584–593.

Heidmann, I., Efremova, N., Saedler, H., and Schwarz-Sommer, Z. (1998). A protocol for transformation and regeneration of *Antirrhinum majus*. *Plant J* 13, 723–728.

Heinrich, B. (1979). Bumblebee Economics. (Harvard University Press, Cambridge, Mass.).

Helsper, J. P. F. G., Davies, J. A., Bouwmeester, H. J., Krol, A. F., and van Kampen, M. H. (1998). Circadian rhythmicity in emission of volatile compounds by flowers of *Rosa hybrida* L. cv. Honesty. *Planta* 207, 88–95.

Henderson, A. (1986). A review of pollination studies in the Palmae. *Bot. Rev.* 52, 221–259.

Henning, J. A., and Teuber, L. R. (1992). Combined gas chromatography-electroantennogram characterization of alfalfa floral volatiles recognized by honeybees (*Hymenoptera: Apidae*). *J. Econ. Entom.* 85, 226–232.

Herdenberger, F., Evrard, J. L., Kuntz, M., Tessier, L. H., Klein, A. L., Steinmetz, A., and Pillay, D. T. N. (1990). Isolation of flower specific cDNA clones from sunflower (*Helianthus annuus* L.). *Plant Sci.* 69,111–122.

Ibrahim, R. K. (1997). Plant O-methyl transferases signatures. *Trends in Plant Sci.* 2, 249–250.

Ibrahim, R. K., Bruneau, A., and Bantignies, B. (1998). Plant O-methyl transferases: molecular analysis, common signature and classification. *Plant Mol. Biol.* 36, 1–10.

Irish, V., and Yamamoto, Y. T. (1995). Conservation of floral homeotic genes function between Arabidopsis and Antirrhinum. *Plant Cell* 7, 1635–1644.

Jones, K. N., Reithel, J. S., and Irvin, R. E. (1998). A trade-off between the frequency and duration of bumblebee visits to flowers. *Oecologia* 117, 161–168.

Joshi, C. P., and Chiang, V. L. (1998). Conserved sequence motifs in plant S-adenosyl-L-methionine-dependent methyl transferases. *Plant Mol. Biol.* 37, 663–674.

Knudsen, J. T., and Tollsten, L. (1993). Trends in floral scent chemistry in pollination syndromes: floral scent composition in moth-pollinated taxa. *Bot. J. Linn. Soc.* 113, 263–284.

Knudsen, J. T., Tollsten, L., and Bergstrom, G. (1993). Floral scents—a checklist of volatile compounds isolated by head-space techniques. *Phytochemistry* 33, 253–280.

Levin, D. A. (1973). The role of trichomes in plant defence. *Quart. Rev. Biol.* 48:3–15.

Loughrin, J. H., Hamilton-Kemp, T. R., Andersen, R. A., and Hildebrand, D. F. (1990). Volatiles from flowers of *Nicotiana sylvestris, N. otophora* and *Malus×Domestica:* Headspace components and day/night changes in their relative concentrations. *Phytochemistry* 29, 2473–2477.

Lutcke, H. A., Chow, K. C., Mickel, F. S., Moss, K. A., Kern, H. F., and Scheele, G. A. (1987). Selection of AUG initiation codons differs in plants and animals. EMBO J. 6, 43–48.

Martin, C., Lister, C., Thijs, H., Prescott, A., Jackson, D., and MacKay, S. (1990). Transposable elements from *Antirrhinum majus*: their uses in gene isolation and characterization. In Plant Biology, Vol. 11: Horticultural biotechnology, A. B. Bennett, and S. D. O'Neill, eds (Wiley-Liss Inc, New York), pp.137–153.

Matile, P., and Altenburger, R. (1988). Rhythms of fragrance emission in flowers. *Planta* 174, 242–247.

Maxwell, C. A., Edwards, R., and Dixon, R. A. (1992). Identification, purification and characterization of S-adenosyl-L-methionine:isoliquiritigenin 2'-O-methyltransferase from alfalfa (*Medicago sativa* L.) *Arch. Biochem. Biophys.* 293,158–166.

McHugh, M. A., and Krukonis, V. J. (1994). Supercritical Fluid Extraction. (Boston, Mass.: Butterworth-Heinemann).

Morrison, J. F., and Ebner, K. E. (1971). Studies on galactosyltransferase. Kinetic investigations with N-acetylglucosamine as the galactosyl group acceptor. *J. Biol. Chem.* 246, 3977–3984.

Murfitt, L. M., Kolosova, N., Mann, C. J. and Dudareva, N. (2000). Purification and characterization of s-adenosyl-L-methionine:benzoic acid carboxyl methyltransferase, the enzyme responsible for biosynthesis of the volatile ester methybenzoate in flowers of *Antirrhinum majus. Arch. Biochem. Biophys.* 381, No. 2 (Sep. 15).

Nielsen, J. K., Jakobsen, H. B., Hansen, P. F. K., Moller, J., and Olsen, C. E. (1995). Asynchronous rhythms in the emission of volatiles from *Hesperis matronalis* flowers. *Phytochemistry* 38, 847–851.

Ohoka, H., Tanaka, S., Wada, K., Kuwabara, T., and Murata, N. (1986). Complete amino acid sequence of 33-kDa protein isolated from spinach photosystem-II particles. *FEBS Lett.* 197, 63–66.

Oka N, Ohishi H, Hatano T, Homberger M, Sakata K, and Watanabe N (1999). Aroma evolution during flower opening in *Rosa damascena* Mill. Z. *Naturforschung,* 54C, 889–895.

Pare, P. W., and Tumlinson, J. H. (1997). De novo biosynthesis of volatiles induced by insect herbivory in cotton plants. *Plant Physiol.* 114:1161–1167.

Pellmyr, O., Bergstrom, G., and Groth, I. (1987). Floral fragrances in Acteae, using differential chromatograms to discern between floral and vegetative volatiles. *Phytochemistry* 26:1603–1606.

Pichersky, E., Lewinsohn, E., and Croteau, R. (1995). Purification and characterization of S-linalool synthase, an enzyme involved in the production of floral scent in *Clarkia breweri. Arch. Biochem. Biophys.* 316, 803–807.

Pichersky, E., Raguso, R. A., Lewinsohn, E., and Croteau, R. (1994). Floral scent production in Clarkia (Onagraceae). I. Localization and developmental modulation of monoterpene emission and linalool synthase activity. *Plant Physiol.* 106, 1533–1540.

Poulton, J. E. (1981). in The Biochemistry of Plants, vol. 7 (Conn, E. E., Ed), pp. 667–723, Academic Press, New York.

Raguso, R. A., and Light, D. M. (1998). Electroantennogram responses of male *Sphinx perelegans* hawkmoths to floral and 'green-leaf' volatiles. *Entom. Experim. Applicata* 86, 287–293.

Raguso, R. A., and Pellmyr, O. (1998). Dynamic headspace analysis of floral volatiles: a comparison of methods. *OIKOS* 81, 238–254.

Raguso, R. A., and Pichersky, E. (1995). Floral volatiles from *Clarkia breweri* and *C. concinna* (Onagraceae): recent evolution of floral scent and moth pollination. *Plant Syst. Evol.* 194, 55–67.

Raguso, R. A., Light, D. M., and Pichersky, E. (1996). Electroantennogram responses of *Hyles lineata* (Sphingidae: Lepidoptera) to volatile compounds from *Clarkia breweri* (Onagraceae) and other moth-pollinated flowers. *J. Chem. Ecology* 22, 1735–1766.

Rodriguez, E. and Levin, D. A. (1976). Biochemical parallelisms of repellants and attractants in higher plants and arthropods. *Recent Adv. Phytochemistry* 111:487–495.

Rose, U. S. R., Manulian, A., Heath, R. R., and Tumlinson, J. H. (1996). Volatile semiochemicals released from undamaged cotton leaves. *Plant Physiol.* 111:487–495.

Ross, J. R., Nam, K. H., D'Auria, J. C., and Pichersky, E. (1999). S-adenosyl-L-methionine:salicylic acid carboxyl methyl transferase, an enzyme involved in floral scent production and plant defense, represents a new class of plant methyl transferases. *Arch. Biochem. Bioiphys.* 367, 9–16.

Sato, F., Tsujita, T., Katagiri, Y., Yoshida, S., and Yamada, Y. (1994). Purification and characterization of S-adenosyl-L-methionine:norcoclaurine 6-O-methyltransferase from cultured *Coptis japonica* cells. *Eur. J. Biochem.* 225,125–131.

Schiestl, F. P., Ayasse, M., Paulus, H. F., Erdmann, D., and Francke, W. (1997). Variation of floral scent emission and post pollination changes in individual flowers of *Ophrys sphegodes* subsp. *Sphegodes. J. Chem. Ecology* 23, 2881–2895.

Seskar, M., Shulaev, V., and Raskin, I. (1998). Endogenous methyl salicylate in pathogen-inoculated tobacco plants. *Plant Physiol* 116:387–392.

Shulaev, V., Silverman, P., and Raskin, I. (1997). Airborne signaling by methyl salicylate in plant pathogen resistance. *Nature* 385:718–721.

Sommer, H., and Saedler, H. (1986). Structure of the chalcone synthase gene of *Antirrhinum majus*. *Mol. Gen. Genet.* 202, 300–305.

Stubbe, H. (1966). Genetik und Zytologie von Antirrhinum L. sect Antirrhinum. (Jena, Germany: VEB Gustav Fisher Verlag), pp. 269–378.

Takabayashi, J., Dicke, M., and Posthumus, M. A. (1994). Volatile herbivore-induced terpenoids in plant mite interactions—variation caused by biotic and abiotic factors. *J. Chem. Ecology* 20, 1329–1354.

Wang, J., and Pichersky, E. (1998). Characterization of Sadenosyl-L-methionine: (iso)eugenol O-methyl transferase involved in floral scent production in *Clarkia breweri*. *Arch. Biochem. Biophys.* 349, 153–160.

Wang, J., Dudareva, N., Bhakta, S., Raguso, R. A., and Pichersky, E. (1997). Floral scent production in*Clarkia breweri* (Onagraceae). II. Localization and developmental modulation of the enzyme S-adenosyl-L-methionine:(iso) eugenol O-methyl transferase and phenylpropanoid emission. *Plant Physiol.* 114, 213–221.

Winter, H., Robinson, D. G., and Heldt, H. W. (1993). Subcellular volumes and metabolite concentrations in barley leaves. *Planta* 191, 180–190.

Yamaguchi, S., Saito, T., Abe, H., Yamane, H., Murofushi, N., and Kamiya, Y. (1996). Molecular cloning and characterization of a cDNA encoding the gibberellin biosynthetic enzyme ent-kaurene synthase B from pumpkin (*Cucurbita maxima* L.) *Plant J.* 10, 203–213.

What is claimed is:

1. An isolated nucleic acid molecule comprising a nucleotide sequence encoding a protein with S-adenosyl-L-methionine:benzoic acid carboxymethyltransferase activity (BAMT), wherein said protein has an amino acid sequence with at least about 50% identity to the amino acid sequence set forth in SEQ ID NO:2.

2. The molecule of claim 1, wherein said protein has at least about 70% identity to the amino acid sequence set forth in SEQ ID NO:2.

3. The molecule of claim 1, wherein said protein has at least about 80% identity to the amino acid sequence set forth in SEQ ID NO:2.

4. The molecule of claim 1, wherein said protein has at least about 90% identity to the amino acid sequence set forth in SEQ ID NO:2.

5. The molecule of claim 1, wherein said protein has the amino acid sequence set forth in SEQ ID NO:2.

6. An isolated nucleic acid molecule, comprising a nucleotide sequence encoding a protein, with S-adenosyl-L-methionine:benzoic acid carboxymethyltransferase activity (BAMT), wherein said nucleotide sequence has at least about 50% identity to the nucleotide sequence set forth in nucleotides 19 to 1110 of SEQ ID NO:1.

7. The molecule of claim 6, wherein said nucleotide sequence has at least about 70% identity to the nucleotide sequence set forth in nucleotides 19 to 1110 of SEQ ID NO:1.

8. The molecule of claim 6, wherein said nucleotide sequence has at least about 80% identity to the nucleotide sequence set forth in nucleotides 19 to 1110 of SEQ ID NO:1.

9. The molecule of claim 6, wherein said nucleotide sequence has at least about 90% identity to the nucleotide sequence set forth in nucleotides 19 to 1110 of SEQ ID NO:1.

10. The molecule of claim 6, wherein said nucleotide sequence encoding the BAMT protein is the nucleotide sequence set forth in nucleotides 19 to 1110 of SEQ ID NO:1.

11. The nucleic acid molecule of claim 6, further comprising a promoter sequence operably linked to the nucleotide sequence encoding the BAMT protein.

12. The molecule of claim 11, wherein said nucleotide sequence has at least about 70% identity to the nucleotide sequence set forth in nucleotides 19 to 1110 of SEQ ID NO:1.

13. The molecule of claim 11, wherein said nucleotide sequence has at least about 80% identity to the nucleotide sequence set forth in nucleotides 19 to 1110 of SEQ ID NO:1.

14. The molecule of claim 11, wherein said nucleotide sequence has at least about 90% identity to the nucleotide sequence set forth in nucleotides 19 to 1110 of SEQ ID NO:1.

15. The molecule of claim 11, wherein said nucleotide sequence is comprised of the sequence set forth in nucleotides 19 to 1110 of SEQ ID NO:1.

16. The molecule of claim 11, wherein said promoter is selected from the group consisting of a constitutive promoter, an inducible promoter, and a cell-specific promoter.

17. The molecule of claim 16, wherein said promoter is a foreign promoter.

18. A host cell comprising the nucleic acid molecule of claim 11.

19. The host cell of claim 18, wherein said nucleotide sequence has at least about 70% identity to the nucleotide sequence set forth in nucleotides 19 to 1110 of SEQ ID NO:1.

20. The host cell of claim 18, wherein said nucleotide sequence has at least about 80% identity to the nucleotide sequence set forth in nucleotides 19 to 1110 of SEQ ID NO:1.

21. The host cell of claim 18, wherein said nucleotide sequence has at least about 90% identity to the nucleotide sequence set forth in nucleotides 19 to 1110 of SEQ ID NO:1.

22. The host cell of claim 18, wherein said nucleotide sequence is set forth in nucleotides 19 to 1110 of SEQ ID NO:1.

23. The host cell of claim 18, wherein said host cell is a eukaryotic cell.

24. The host cell of claim 23, wherein said eukaryotic cell is a plant cell.

25. The host cell of claim 18, wherein said host cell is a prokaryotic cell.

26. The host cell of claim 25, wherein said prokaryotic cell is a bacterial cell.

27. A transgenic plant comprising the nucleic acid molecule of claim 11.

28. The transgenic plant of claim 27, wherein said promoter is a foreign promoter.

29. The transgenic plant of claim 27, wherein said nucleotide sequence has at least 70% identity to the nucleotide sequence set forth in nucleotides 19 to 1110 of SEQ ID NO:1.

30. The transgenic plant of claim 27 wherein said nucleotide sequence has at least 80% identity to the nucleotide sequence set forth in nucleotides 19 to 1110 of SEQ ID NO:1.

31. The transgenic plant of claim 27 wherein said nucleotide sequence has at least 90% identity to the nucleotide sequence set forth in nucleotides 19 to 1110 of SEQ ID NO:1.

32. The transgenic plant of claim 27, wherein said nucleotide sequence is set forth in nucleotides 19 to 1110 of SEQ ID NO:1.

33. A method of expressing a BAMT protein, said method comprising the step of:

(a) introducing into a host cell the nucleic acid molecule of claim 11, and (b) culturing under conditions to achieve expression of said protein.

34. The method of claim 33, wherein said nucleotide sequence has at least about 70% identity to the nucleotide sequence set forth in nucleotides 19 to 1110 of SEQ ID NO:1.

35. The method of claim 33, wherein said nucleotide sequence has at least about 80% identity to the nucleotide sequence set forth in nucleotides 19 to 1110 of SEQ ID NO:1.

36. The method of claim 33, wherein said nucleotide sequence has at least about 90% identity to the nucleotide sequence set forth in nucleotides 19 to 1110 of SEQ ID NO:1.

37. The method of claim 33, wherein said nucleotide sequence is set forth in nucleotides 19 to 1110 of SEQ ID NO:1.

38. The method of claim 33, wherein said host cell is a eukaryotic cell.

39. The method of claim 38, wherein said host cell is a plant cell.

40. The method of claim 33, wherein said host cell is a bacterial cell.

41. An isolated nucleic acid molecule comprising a nucleotide sequence encoding a protein with S-adenosyl-L-methionine:benzoic acid carboxymethyltransferase activity (BAMT), wherein said nucleotide sequence hybridizes under moderately stringent conditions to the nucleotide sequence given in the nucleotides 19 to 1110 of SEQ ID NO:1, wherein moderately stringent hybridization conditions comprise prewashing with a 5×SSC solution, 0.5% sodium dodecyl sulfate (SDS), 1.0 mM ethylene diaminetetraacetic acid (pH 8.0) and hybridization and washing conditions of 55° C., 5×SSC.

42. The isolated nucleic acid molecule of claim 41 wherein the nucleotide sequence encoding a BAMT protein has at least 70% nucleotide sequence identity with nucleotides 19–1110 of SEQ ID NO:1.

43. The isolated nucleic acid molecule of claim 41 wherein the nucleotide sequence encoding a BAMT protein has at least 80% nucleotide sequence identity with nucleotides 19–1110 of SEQ ID NO:1.

44. The isolated nucleic acid molecule of claim 41 wherein the nucleotide sequence encoding a BAMT protein has at least 90% nuclebtide sequence identity with nucleotides 19–1110 of SEQ ID NO:1.

* * * * *